US010413287B2

(12) United States Patent
Heiges et al.

(10) Patent No.: US 10,413,287 B2
(45) Date of Patent: *Sep. 17, 2019

(54) SURGICAL DILATOR, RETRACTOR AND MOUNTING PAD

(71) Applicant: BHDL Holdings, LLC, Atlanta, GA (US)

(72) Inventors: Bradley A. Heiges, Savannah, GA (US); David E. Lane, II, Atlanta, GA (US)

(73) Assignee: BHDL Holdings, LLC, Atlanta, GA (US)

( * ) Notice: Subject to any disclaimer, the term of this patent is extended or adjusted under 35 U.S.C. 154(b) by 98 days.

This patent is subject to a terminal disclaimer.

(21) Appl. No.: 15/619,784

(22) Filed: Jun. 12, 2017

(65) Prior Publication Data

US 2017/0333021 A1    Nov. 23, 2017

Related U.S. Application Data

(60) Continuation-in-part of application No. 14/838,599, filed on Aug. 28, 2015, now Pat. No. 9,675,334,
(Continued)

(51) Int. Cl.
*A61B 17/02* (2006.01)
*A61B 17/34* (2006.01)
(Continued)

(52) U.S. Cl.
CPC ............ *A61B 17/0218* (2013.01); *A61B 1/32* (2013.01); *A61B 17/025* (2013.01);
(Continued)

(58) Field of Classification Search
CPC . A61B 17/34; A61B 17/3423; A61B 17/3439; A61B 17/02; A61B 17/0218; A61B 1/32; A61M 29/00
See application file for complete search history.

(56) References Cited

U.S. PATENT DOCUMENTS 3,788,318 A   1/1974  Kim et al.
3,807,393 A   4/1974  McDonald
(Continued)

FOREIGN PATENT DOCUMENTS

EP         1832241         9/2007
WO    WO2004032726        4/2004
(Continued)

*Primary Examiner* — Christopher J Beccia
(74) *Attorney, Agent, or Firm* — McHale & Slavin, P.A.

(57) ABSTRACT

A retractor having an elongated body that provides access to a surgical location within a patient. The elongate body includes a plurality of segments that are connected to one another through a plurality of ratcheting mechanisms. The ratcheting mechanisms permit relative movement of the segments with respect to one another when expander dilators are inserted within the retractor. The segments are surrounded and retained by a resilient elastomeric sleeve or bands. The distal end surfaces of the segments include thin edges that are configured to mobilize, dissect, split and retract the terminal tissues in the surgical area. The retractor may be used in conjunction with a shim.

37 Claims, 45 Drawing Sheets

Related U.S. Application Data which is a continuation-in-part of application No. 14/524,811, filed on Oct. 27, 2014, now Pat. No. 9,585,648, which is a continuation of application No. 13/932,735, filed on Jul. 1, 2013, now Pat. No. 8,870,760, which is a division of application No. 12/541,617, filed on Aug. 14, 2009, now Pat. No. 8,480,704, which is a continuation-in-part of application No. 12/393,352, filed on Feb. 26, 2009, now abandoned.

(51) Int. Cl.
*A61M 29/00* (2006.01)
*A61B 1/32* (2006.01)
*A61B 90/30* (2016.01)
*A61B 17/00* (2006.01)
*A61B 90/00* (2016.01)

(52) U.S. Cl.
CPC ...... *A61B 17/0293* (2013.01); *A61B 17/3423* (2013.01); *A61B 17/3439* (2013.01); *A61M 29/00* (2013.01); *A61B 17/02* (2013.01); *A61B 2017/00039* (2013.01); *A61B 2017/00407* (2013.01); *A61B 2017/0256* (2013.01); *A61B 2017/3419* (2013.01); *A61B 2017/3488* (2013.01); *A61B 2090/306* (2016.02); *A61B 2090/3966* (2016.02)

(56) References Cited

U.S. PATENT DOCUMENTS

| | | | |
|---|---|---|---|
| 5,201,756 A | 4/1993 | Horzewski et al. | |
| 5,345,927 A * | 9/1994 | Bonutti | A61B 17/0218 600/204 |
| 5,460,170 A | 10/1995 | Hammerslag | |
| 5,797,951 A | 8/1998 | Mueller | |
| 5,976,146 A * | 11/1999 | Ogawa | A61B 17/00234 604/174 |
| 6,187,000 B1 | 2/2001 | Davison et al. | |
| 6,354,995 B1 | 3/2002 | Hoftman et al. | |
| 6,524,320 B2 | 2/2003 | DiPoto | |
| 6,652,553 B2 | 11/2003 | Davison et al. | |
| 7,144,393 B2 | 12/2006 | DiPoto et al. | |
| 7,179,225 B2 | 2/2007 | Shluzas et al. | |
| 7,221,451 B2 | 5/2007 | Ohtake et al. | |
| 7,223,233 B2 | 5/2007 | Branch et al. | |
| 7,261,688 B2 | 8/2007 | Smith et al. | |
| 7,604,648 B2 * | 10/2009 | Kerr | A61B 17/0218 606/15 |
| 8,480,704 B2 | 7/2013 | Heiges et al. | |
| 9,028,522 B1 | 5/2015 | Prado | |
| 9,066,701 B1 | 6/2015 | Finley et al. | |
| 9,675,334 B2 * | 6/2017 | Heiges | A61B 17/0218 |
| 2003/0069477 A1 | 4/2003 | Raisman et al. | |
| 2003/0191371 A1 | 10/2003 | Smith et al. | |
| 2005/0021562 A1 | 1/2005 | Idei et al. | |
| 2005/0215862 A1 | 9/2005 | Larson et al. | |
| 2006/0041270 A1 | 2/2006 | Lenker et al. | |
| 2006/0089536 A1 | 4/2006 | Perez-Cruet et al. | |
| 2006/0200023 A1 | 9/2006 | Melkent et al. | |
| 2006/0229636 A1 | 10/2006 | Woodburn, Sr. et al. | |
| 2007/0021656 A1 | 1/2007 | Martin et al. | |
| 2007/0060939 A1 | 3/2007 | Lancial et al. | |
| 2007/0129608 A1 | 6/2007 | Sandhu | |
| 2008/0146885 A1 | 6/2008 | Protopsaltis | |
| 2008/0234550 A1 | 9/2008 | Hawkes et al. | |
| 2009/0124860 A1 | 5/2009 | Miles et al. | |
| 2009/0287060 A1 | 11/2009 | Pell et al. | |
| 2010/0022844 A1 | 1/2010 | Mangiardi | |
| 2010/0217088 A1 | 8/2010 | Heiges et al. | |
| 2010/0217090 A1 | 8/2010 | Heiges et al. | |

FOREIGN PATENT DOCUMENTS

| | | |
|---|---|---|
| WO | WO2006049917 | 5/2006 |
| WO | WO2015191836 | 12/2015 |

* cited by examiner

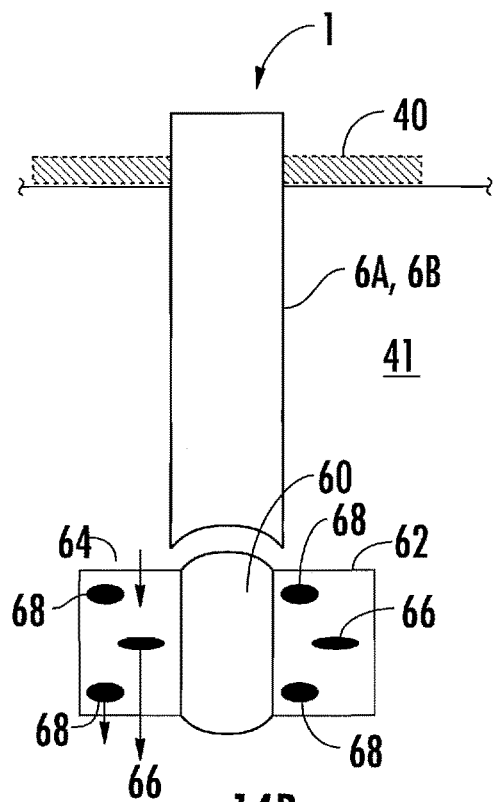
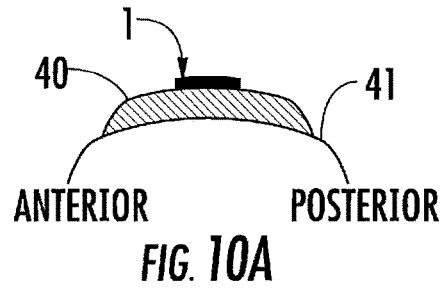
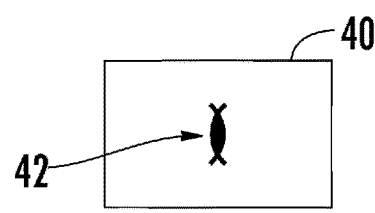
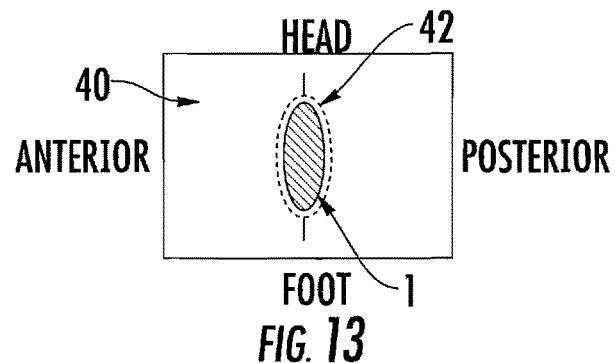
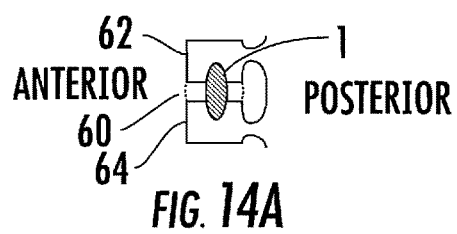

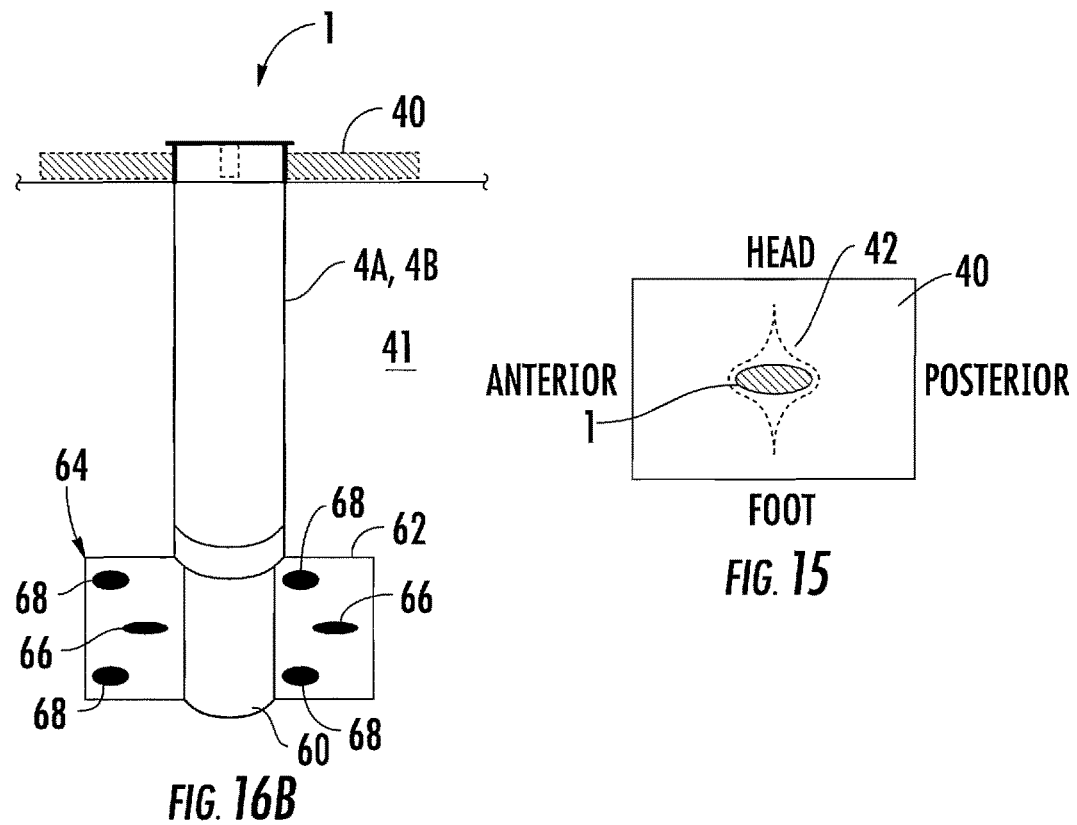
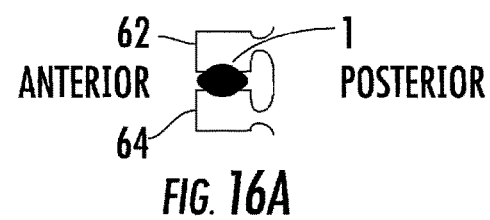
FIG. 16A

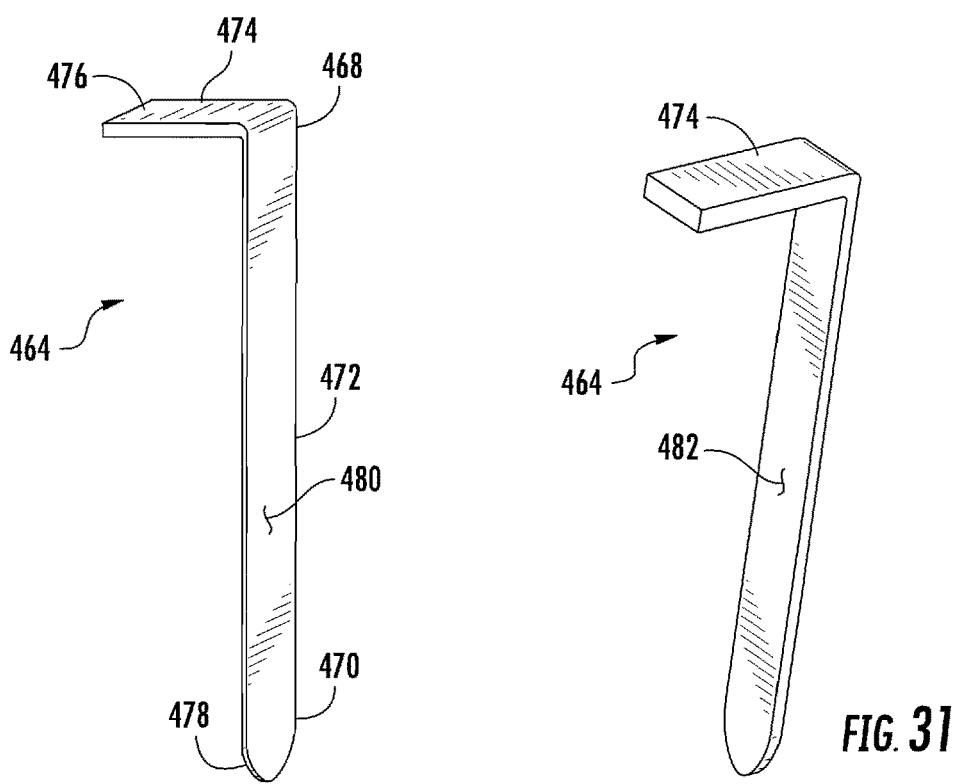
FIG. 30
FIG. 31
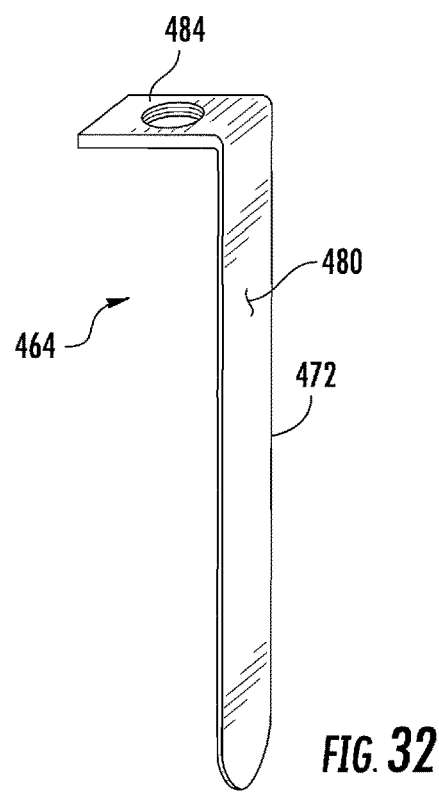
FIG. 32

SURGICAL DILATOR, RETRACTOR AND MOUNTING PAD

CROSS-REFERENCE TO RELATED APPLICATIONS

In accordance with 37 C.F.R. § 1.76, a claim of priority is included in an Application Data Sheet filed concurrently herewith. Accordingly, the present invention claims priority as a continuation-in-part of U.S. patent application Ser. No. 14/838,599, entitled "Surgical Dilator, Retractor and Mounting Pad", filed Aug. 28, 2015, which application is a continuation-in-part of U.S. patent application Ser. No. 14/524,811, entitled "Surgical Dilator, Retractor and Mounting Pad", filed Oct. 27, 2014, now U.S. Pat. No. 9,585,648, issued Mar. 7, 2017, which application is a continuation of U.S. patent application Ser. No. 13/932,735, entitled "Surgical Dilator, Retractor and Mounting Pad", filed Jul. 1, 2013, now U.S. Pat. No. 8,870,760, issued Oct. 28, 2014, which application is a divisional of U.S. patent application Ser. No. 12/541,617, entitled "Surgical Dilator, Retractor and Mounting Pad", filed Aug. 14, 2009, now U.S. Pat. No. 8,480,704, issued Jul. 9, 2013, which application is a continuation-in-part of U.S. patent application Ser. No. 12/393,352, entitled "Retractor and Mounting Pad", filed Feb. 26, 2009, now abandoned, the entire contents of which are hereby expressly incorporated by reference.

FIELD OF THE INVENTION

The present system and method relate to devices and methods for performing percutaneous surgeries, and in particular, to a less invasive access portal for use in orthopedic spinal surgery.

BACKGROUND OF THE INVENTION

Open spinal surgical procedures generally require a relatively long incision, extensive muscle stripping, prolonged retraction of tissues, and increase risk of damage to vascular and nerve tissue. This type of procedure usually necessitates many weeks of post-operative recovery due to the use of long hours under general anesthesia, blood transfusions and the unavoidable trauma caused to the body tissues during the procedures. An open surgical procedure will also result in significant permanent scarring leading to fusion disease.

Surgery performed percutaneously has achieved major improvements over open surgery. The reduction of muscle and tissue dissection significantly reduces post operative recovery, pain, and recovery time. Percutaneous surgery is particularly beneficial for spinal surgery because the surgical area is deep within the body and in locations surrounded by sensitive and critical body tissues. Tube retractors have been developed to provide minimally invasive access to the surgical area. The ability to dilate muscle tissue, as opposed to strip or detach them from the bony anatomy, will reduce the damage and risks normally associated with the open type surgery.

The typical tube retractor technique starts with the identification of the correct entry point, establishing the trajectory from the skin to the pathology to be addressed and the corresponding skin incision. The initial soft tissue dilator is inserted through the incision and forcefully advanced to the objective site. A series of larger dilators are inserted over the initial dilator thereby sequentially increasing the diameter until the final/operative dilator is inserted. Once the operative dilator is in place it must be fixed in order to resist movement that will result from forces imposed by the patient's tissue. Currently, the accepted approach to fixation is a point outside of the patient's anatomy. Typically a rigid arm is attached at one end to the retractor while the opposite end of the arm is attached to a bed rail clamp. Once the retractor is fixed in position, the surgeon begins the operation to address the pathology. Upon completion of the procedure the retractor tube is removed and the skin incision is closed. Because of the reduced morbidity to the patient, the patient's initial recovery time should be less, blood loss should be less, operating room time should be less, anesthesia time should be less, patient stay in the hospital should be less, return to work time should be less and the overall cost of the procedure should be less.

One of the most difficult aspects of the current technique is that the rigid fixation of the retractor is sometimes subject to unintentional or unavoidable movement of the patient during the course of the surgical procedure. Another consistent problem is the inability of the current designs and methods to adequately retract the muscle tissue at the distal end of the retractor, which for all intents and purposes is the most crucial portion of the retractor. Due to the retractors inability to clear the surgical area the surgeon must resort to cutting, cauterizing and removing the final fibers of muscle. This process of physical tissue removal carries with it increased risk of damage to ancillary tissues and nervous tissues, while at the same time increasing morbidity, blood loss and operative time. These difficulties result in high levels of frustration making the technique less likely to be adopted by the majority of surgeons. The current retractors lack the distraction capability at the distal end of the retractor which is where the strongest forces resisting the retractor are present. In addition the current retractor designs do not accommodate the natural anatomical shape of the patient's anatomy where the pathology exists.

DESCRIPTION OF THE PRIOR ART

Retractors for use in percutaneous spinal surgery lack the ability to easily efficiently and clearly access the surgical area. Likewise, they do not have a simple, effective and efficient device to anchor the retractor relative to the patient.

U.S. Pat. No. 5,460,170 discloses an adjustable, expandable retractor suitable for use in small surgical incisions or punctures. The device is able to expand the incision or puncture to one or more enlarged cross-sectional areas and designed to protect the edges of the incision or puncture. The surgical retractor comprises a radially expandable tubular body having a control at the proximal end. Pull wires couple the control to the tubular body such that force applied to the control is transmitted to the tubular body as an axially compressive force.

U.S. Pat. No. 3,788,318 discloses an expandable tube, referred to therein as a cannula, is formed by arranging at least one sheet of thin flexible material to form a tube while providing teeth or the like on the interengaging surfaces to permit controlled expansion of the tube by adjusting the surfaces over one another.

U.S. Pat. No. 6,187,000 discloses a cannula with an expandable portion for enabling an increase in the cross-sectional area of the passage at the distal end. The expandable portion of the tube structure, when expanded, has a conical configuration.

U.S. Pat. No. 6,652,553 discloses a surgical tool for use in expanding a cannula and includes a first leg having a first end engageable with an inner surface of the cannula. A second leg is connected with the first leg. The second leg has a second end engageable with the inner surface of the cannula. The first and second ends are movable away from each other to apply a radially outwardly directed force to the inner surface of the cannula and cause expansion of the cannula.

U.S. Pat. No. 7,261,688 discloses a retractor having a working channel formed by a first portion coupled to a second portion. The first and second portions are movable relative to one another from an unexpanded configuration to an expanded configuration to increase the size of the working channel along the length thereof.

U.S. Pat. Nos. 6,524,320 and 7,144,393 disclose a cannula having an expandable portion for enabling an increase in the cross-sectional area of the passage. The expandable portion of the tubular structure has a slot and a guide member disposed in the slot. The guide member is movable from a first end of the slot toward a second end of the slot to enable the cross-sectional area of the passage to increase. The expandable portion has a stop between the first and second ends of the slot engageable with the guide member to retain the guide member in a position relative to the slot and resist movement of the guide member from the position relative to the slot. In the '393 patent, the expandable portion has a contracted condition in which the cross-sectional area of the distal end of the passage has a first cross-sectional area. The expandable portion has an expanded condition in which the distal end of the passage has a second cross-sectional area greater than the first cross-sectional area. The second cross-sectional area is greater than a cross-sectional area of the proximal end of the passage when the expandable portion is in the expanded condition. A retaining mechanism resists movement of the expandable portion from the expanded condition toward the contracted condition during the surgical procedure. The retaining mechanism is released at the conclusion of the surgical procedure to permit movement of the expandable portion from the expanded condition toward the contracted condition for removal of the structure. The expandable sleeve is provided with a lockable means in the expanded position.

U.S. Pat. Nos. 7,179,225 & 7,221,451 disclose a retractor that has an elongate body and an expandable shroud. The elongate body has an outer surface and an inner surface partially defining a passage. The elongate body also has a first longitudinal edge and a second longitudinal edge. The elongate body is capable of having an enlarged configuration when inserted within the patient. In the enlarged configuration the first longitudinal edge is spaced apart from the second longitudinal edge. The expandable shroud is configured to extend from the first longitudinal edge to the second longitudinal edge when the first and second edges are spaced apart. The shroud partially defines the passage. The cross-sectional area of said passage at a first location is greater than the cross-sectional area of the passage at a second location, wherein the first location is distal to the second location. See FIG. 70 in the '225 patent and FIG. 71 for oval and oblong shape.

U.S. Pat. No. 7,223,233 discloses methods and devices for illuminating a surgical space in a patient. A retractor provides a portal or working path for access to a working space location in the patient. The retractor transmits and emits light from a light delivery system to illuminate the working channel and surgical space.

U.S. Publication No. 2006/0041270 discloses an expandable sheath that is insertable into a patient through an incision. Once inserted and advanced to the target surgical site, the sheath can be expanded to an enlarged diameter. The wall of the sheath is fabricated from a tubular structure comprising filamentous elements that extend axially and at least partially circumferentially along the length of the sheath. The tubular filamentous material is drawn or expanded axially to create the small diameter configuration that is inserted into the patient. A standoff attaches the distal end of the tubular filamentous material to the sheath hub by way of radially movable anchors. Additional filamentous tubular material extends out the proximal end of the hub. A compression mechanism forces the additional filamentous tubular material in the distal direction which causes axial compression and radial or diametric dilation of the working length of the sheath, that part of the sheath that extends beyond the proximal end of the hub. Radial dilation is accomplished with no substantial change in sheath working length.

U.S. Publication No. 2006/0200023 discloses systems and methods include an anchor engageable to a vertebra and an extender removably mounted to the anchor. The extender includes an insulating member extending at least partially thereabout to electrically insulate the extender and prevent shunting of electrical signals delivered through the extender to the anchor to structures adjacent the extender. Flexible jacket 26 includes a means for monitoring nerves.

U.S. Publication No. 2008/0234550 discloses a less invasive access port for use in minimally invasive surgery allows for manipulation of the viewing angle into the working site in a transverse plane. According to one exemplary embodiment, the less invasive access port is designed to minimize the need for muscle retraction. Additionally, the less invasive access portal provides sufficient light, irrigation, suction and space for sundry medical instruments. According to one exemplary embodiment, a less invasive access port device includes a retractor assembly having four retractor blades secured in various positions by pins placed within slots on the retractor blades. A cannula includes integrated interfaces for light, irrigation and suction. A housing forms a collar around a top of the cannula and houses the light, irrigation and suction mechanisms. Instruments and implants may be passed through the cannula and into the working space created by the retractor assembly. Visualization of the working site can be attained under direct vision.

SUMMARY OF THE INVENTION

The present invention is directed to methods and devices for performing percutaneous, minimally invasive spinal surgery. In particular the invention includes a percutaneous tissue retraction device that provides access to the surgical area within the patient. Another aspect of the invention includes a device for anchoring the retractor device directly on the patient without the aid of additional structural elements to affix the retractor to other objects within the operating room such as the operating table.

The current retractor addresses the current problem making its utilization more reproducible, easier to learn and visualize and increases safety while delivering a more consistent result.

The anchoring device includes a pad that is affixed to the patient. Should the patient move slightly, intentionally or unintentionally, the retractor maintains the same tissue retraction and the same trajectory. This provides an accurate and stable portal to the patient's pathology. The pad eliminates the necessity for rigid fixation to a point outside of the field of operation or to an independent immobile point such as a bed rail. The rigid fixation device is metallic and used with conventional metallic split blade retractors that reduce visualization of the approach through the retractor as well as the visualization of the objective site while using operative fluoroscopy.

The anatomical shape of the distal end of the current retractor produces a significantly improved ability to mobilize, dissect, split and retract the terminal tissues of the psoas muscle at the point on the spine where the entry is to be made. Current distal end designs are parallel to the spine and do not comply with the natural shape of the spine.

The ovoid shape of the retractor requires less retraction in two different planes while achieving adequate exposure thereby making the procedure easier and more reproducible.

Likewise, the anatomical shape of the distal end of the dilator when inserted safely and gently, divides/splits the psoas muscle fibers along the longitudinal plane of the spine. The distal end shape of the dilator mobilizes and dissects the muscle fibers more effectively and when subsequently rotated ninety degrees provides a dilator that will safely and gently sweep the terminal fibers in order to enable consistent retraction of the muscle fibers while the retractor is inserted. The final dilator is unique in its ability to create a path for the retractor which complies with the patient's anatomy in a safe, gentle fashion allowing for efficient mobilization of the muscle fibers and maintaining the muscle retraction when inserting the retractor. Current systems use round dilators with flat bottom surfaces. When the retractor is inserted over the final dilator and the dilator is removed, muscle fibers creep under the end of the retractor and the doctor must then use instruments to sweep the fibers out of the way, under the blades or ablate them.

Accordingly, it is an objective of the instant invention to provide a retractor for performing minimally invasive spinal surgery that provides improved access to the surgical area.

It is a further objective of the instant invention to provide a retractor device that the surgeon will find more intuitive to use owing to its construction ease of use.

It is yet another objective of the instant invention to provide a retractor for minimally invasive spinal surgery with an anatomically shaped distal end resulting in a much improved ability to mobilize, dissect, split and retract the terminal tissues of the psoas muscle at the point of the spine where the entry is to be made.

It is a still further objective of the invention to provide a retractor where the walls of the retractor apply an opening force throughout the length of the retractor and provide a more robust retraction.

It is a still further objective of the invention to provide a radiolucent retractor for greater visualization during the surgical procedure.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 10A is a side view of a patient with their side in an upward position and patient pad and retractor in place.

FIG. 10B is a top view of the patient pad with the initial incision.

FIG. 13 is a top view of the retractor in position on the patient.

FIG. 14A is a top view of the retractor in position within the patient's body.

FIG. 14B is a side view of the retractor positioned within the patient's body.

FIG. 15 is a top view of the retractor in position within the patient's body after being rotated ninety degrees.

FIG. 16A is a top view of the retractor in position within the patient's body after being rotated ninety degrees.

FIG. 16B is a side view of the retractor positioned within the patient's body after being rotated ninety degrees.

FIG. 30 is a front side perspective view of a retractor shim.

FIG. 31 is a back side perspective view of a retractor shim.

FIG. 32 is a perspective view of the retractor shim configured to be table mounted.

DETAILED DESCRIPTION OF THE INVENTION

The present invention is directed to methods and devices for performing percutaneoous surgery and in particular spinal surgery. The surgery is performed through a portal or passageway provided by a retractor. The retractor is expandable in situ to thereby increase the size of the surgical area as well as the access thereto. It is particularly constructed to minimize trauma to tissue surrounding the retractor and the surgical area. The retractor can be used with any surgical approach to the spine such as; lateral, postero-lateral and/or antero-lateral, anterior, posterior, posterior mid-line, and in other regions of the body not associated with the spine.

Figure 1:
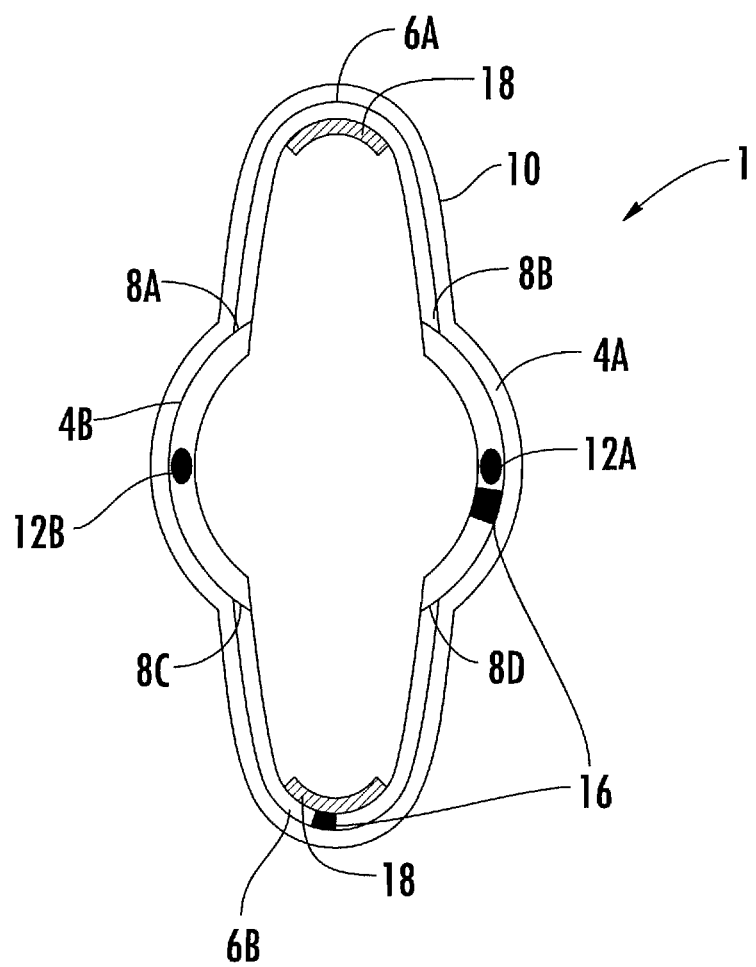
FIG. 1 is a top view of the retractor showing the retractor segments and the encircling elastomeric sleeve.

FIG. 1 is a top view of retractor 1. As shown retractor 1 is comprised of four discrete segments. As shown, the segments consist of a pair of opposing semi cylindrical members 4A and 4B as well as a pair of opposing semi elliptical members 6A and 6B. A ratcheting mechanism 8A and 8C is located at each of the junctions between opposing semi cylindrical member 4B and opposing semi elliptical members 6A and 6B. Likewise a ratcheting mechanism 8B and 8D is located at each of the junctions between semi cylindrical segment 4A and opposing semi elliptical members 6A and 6B. The four segments once assembled and surrounded by a silicone sleeve 10 form a single working unit that is generally elongated and oval shaped in cross section. The sleeve 10 conforms to the shape of the exterior surfaces of the segments and extends the entire length of the segments from the proximal end, the top portion, to the distal end, bottom portion and exerts a radially directed inward force against segments 4A, 4B, 6A and 6B. The assembly thereby forms an elongated ovoid shaped retractor wherein the parallel distraction will occur along the length of the retractor based upon the engagement and disengagement of the teeth placed along the longitudinal axis of the retractor. While shown and described as having four segments the retractor could be formed as two segments each including a semi cylindrical segment and a semi elliptical segment.

The segments 4A, 4B, 6A and 6B are formed from plastic or any other suitable radio lucent material. Segments 4A and 4B each respectively have screw holes 12A and 12B designed to receive a bone screw for distal fixation of the retractor to a vertebral body. The segments also contain insulated electrical conductors 16 included in the walls of the segments. The conductors 16 terminate at the proximal and distal surfaces of the segments with exposed electrical contacts to provide an electrical pathway for nerve monitoring Also included within the segments are internal tracks for mounting fiber optical lights 18 to provide illumination of the surgical space located at the distal end of the retractor. Each of the segments 4A, 43, 6A, and 6B may contain radio opaque markers 24 to enable visualization throughout the procedure.

Figure 2:
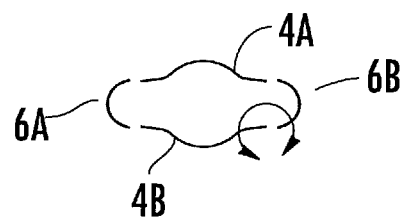
FIG. 2 is a schematic showing the four segments of the retractor.
Figure 3:
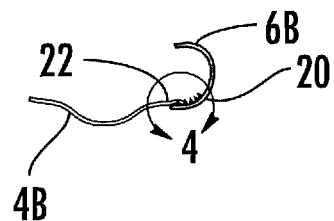
FIG. 3 is enlarged top sectional view of two of the segments and ratcheting mechanism on each of the segments within the circled area of FIG. 2.
Figure 5:
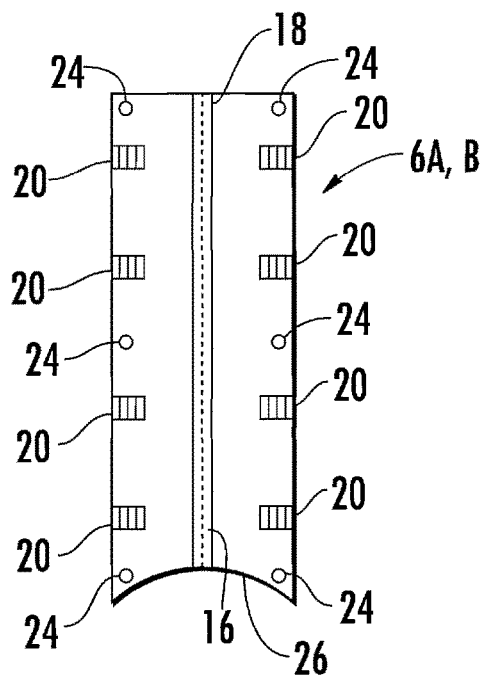
FIG. 5 is a front view of the interior surface of one of the semi cylindrical members showing four discrete locations for the teeth which form part of the ratcheting mechanism.
Figure 6:
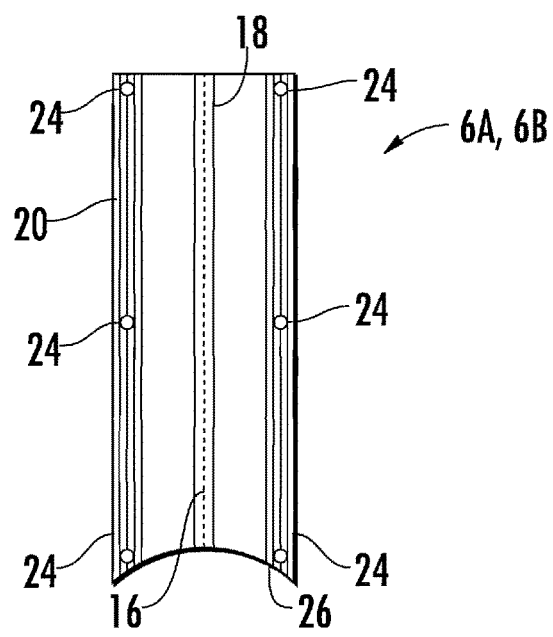
FIG. 6 is a front view of the interior surface of one of the semi cylindrical showing a continuous set of teeth that run the length of the segment from the proximal to the distal end portions.

FIG. 2 shows a partially exploded top view of the four segments prior to engagement via the ratcheting mechanisms. FIG. 3 is an enlarged view of the encircled area of FIG. 2. As can be seen in FIG. 3 semi-circular segments have teeth or grooves 20 located on the interior surface adjacent both edges of the semi circular segments 6A and 6B. These teeth or grooves 20 are located at four separate points along the length of the segments between the proximal and distal end portions as shown in FIG. 5. Alternatively teeth or grooves 20 can run the entire length of the segments from the distal end portion to the proximal end portion as shown in FIG. 6. As seen from the front view, the lower distal end surface of segments 6A and 6B form a concave edge 26.

Figure 4:
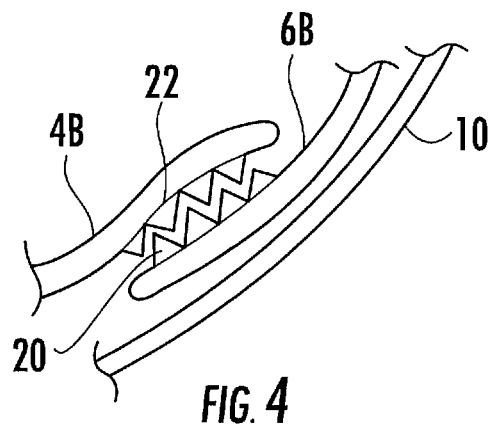
FIG. 4 is an enlarged top partial sectional view showing the interengaing teeth of the ratcheting mechanism on each of the segments and the surrounding elastomeric sheath within the circled area of FIG. 3.
Figure 7:
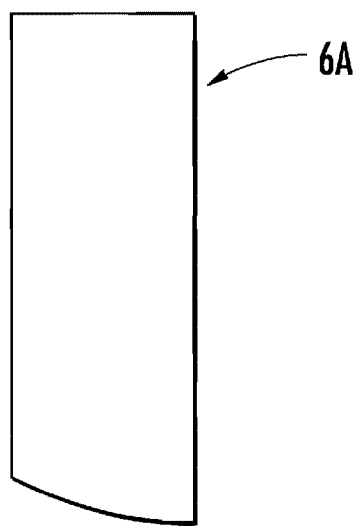
FIG. 7 is a side view of the exterior surface of one of the semi cylindrical segments.
Figure 8:
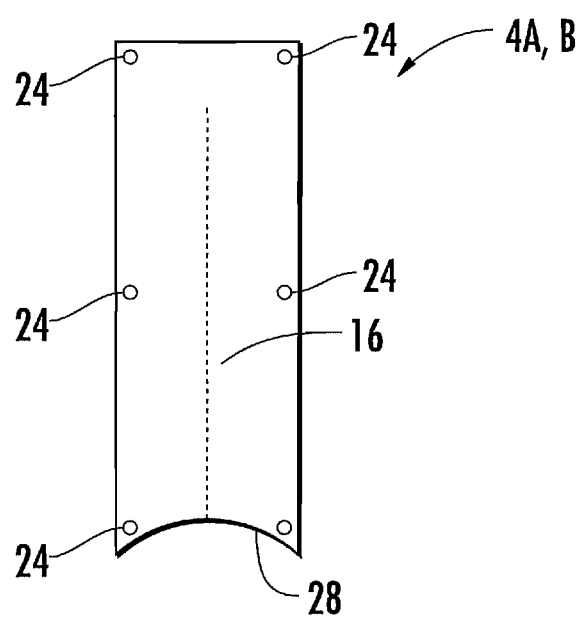
FIG. 8 is a front view of the exterior surface of one of the semi elliptical segments.
Figure 9:
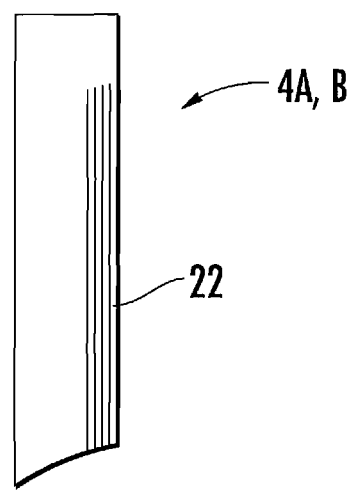
FIG. 9 is a side view of the exterior surface of one of the semi elliptical segments.
Figure 11A:
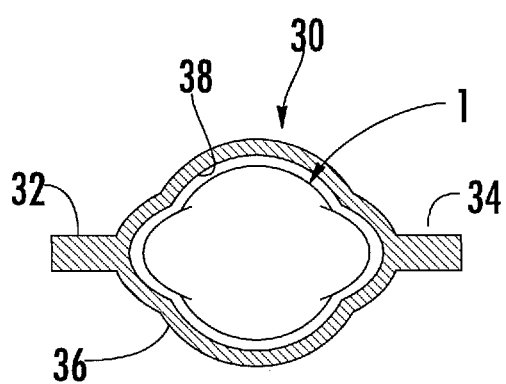
FIG. 11A is a top view of the tool that is used to rotate the final operative dilator as well as the retractor.
Figure 11B:
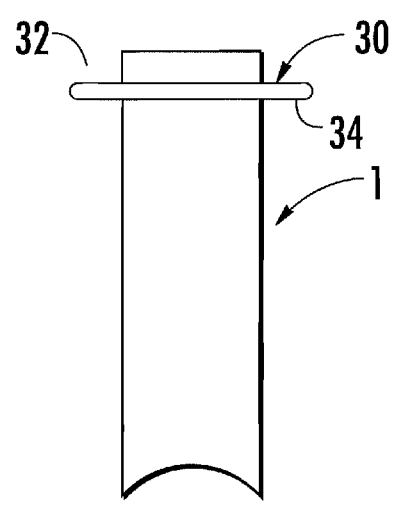
FIG. 11B is a side view of the tool that is used to rotate the final operative dilator as well as the retractor.

FIG. 7 shows a side view of the external surface of the semi cylindrical segments 6A and 6B. FIG. 8 is a front view of the exterior surface of one of the semi elliptical members 4A and 4B. As seen from the front view the lower distal end surface of segments 4A and 4B form a convex edge 28. Concave edges 26 and convex edges 28 form a tip at the distal end of the retractor 1 that is anatomical in shape and particularly configured to significantly improve the ability to mobilize, dissect, split and retract the terminal tissues of the psoas muscle at the point on the spine where the entry is to be made. FIG. 9 is an exterior surface side view of one of the semi elliptical members 4A and 4B. One or both of the segments 4A and 6B contain an insulated electrical conductor 16 included in the walls of the segments. A tool 30, shown in FIGS. 11A and 11B is used to facilitate a ninety degree rotation of the retractor as will be explained below. The tool 30 includes a pair of diametrically opposed handles 32 and 34 that are each connected to an annular member 36. The inner surface 38 of the annular member 36 is configured to operatively cooperate with the external surface of sleeve 10 surrounding the retractor 1 adjacent the top portion thereof. Semi elliptical segments 4A and 4B have complimentary teeth or grooves 22. Teeth or grooves are located on the exterior of semi elliptical segments 4A and 4B adjacent each of the edges of semi elliptical segments 4A and 4B. Teeth or grooves 22 extend the entire length of the segments form the proximal to distal end portion as shown in FIG. 9. FIG. 4 shows one of the ratcheting mechanisms 8A-8D and the inter engagement of teeth 20 and 22 as well as sleeve 10 which exerts a radially directed inward force on each of the retractor segments.

The present system is a patient based retractor that does not require fixation to an articulating arm. The patient based retractor includes a pad 40 that eliminates the necessity for a rigid fixation to a point outside of the field of operation or to an independent immobile point such as a bed rail. The pad 40 is applied to the sterilized area on the patient's body 41. The physical properties of the material including its size, thickness and composition cause significant friction, or adhesion, between the pad and the sterile site on the patient's skin. By way of example, FIGS. 10A and 10B illustrate the pad 40 in a deployed position. This can be reinforced with the application of tape and or IOBAN® if necessary. By way of example the pad can be formed from a polyurethane material. While the pad 40 and retractor 1 have been shown for use during minimally invasive spinal surgery it should be understood that the anchoring pad 40 could be used in combination with retractor 1 or a retractor of any configuration and for other types of surgery as well, such as laparoscopic gal bladder surgery or appendectomy.

Figures 12A, 12B:
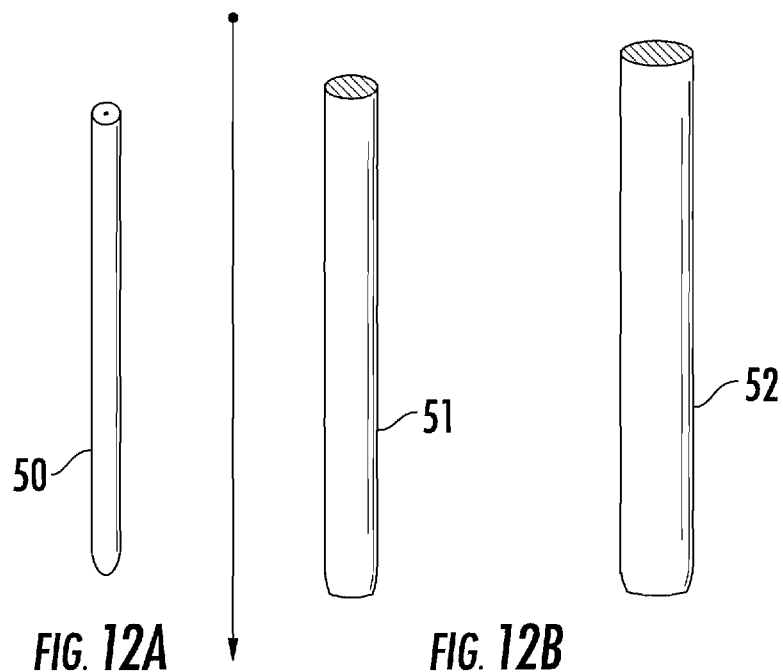
FIGS. 12A and 12B illustrate the initial dilators.
Figure 12G:
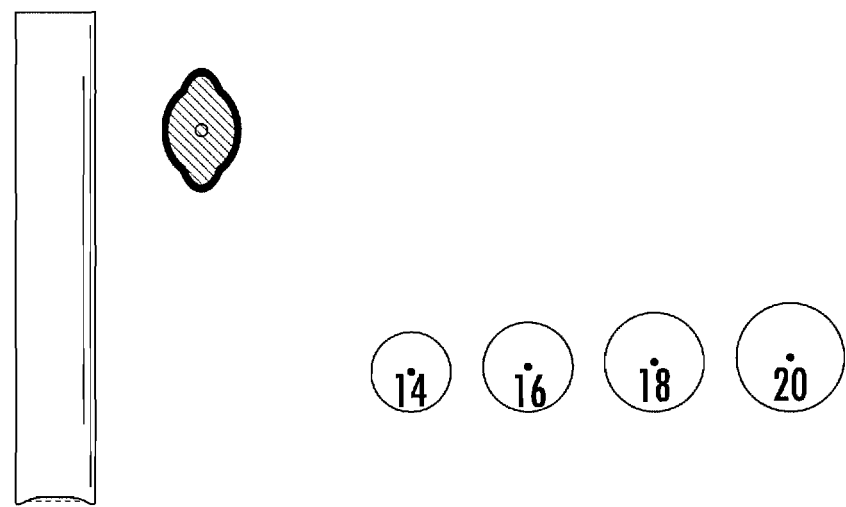
FIG. 12G is an example of a retractor expansion dilator.
Figure 12C:
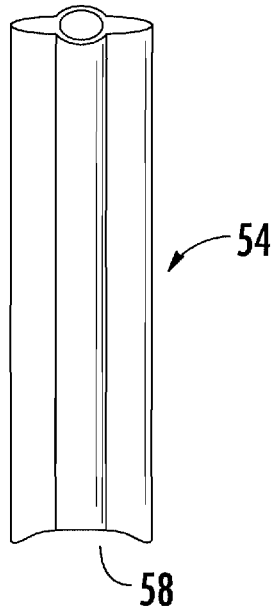
FIGS. 12C, 12D, 12E and 12F illustrate various views of the oblong final operative dilator.
Figure 12E:
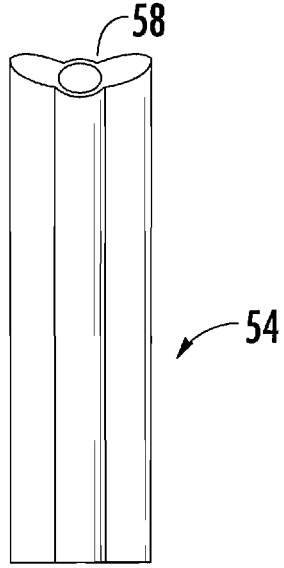
Figure 12F:
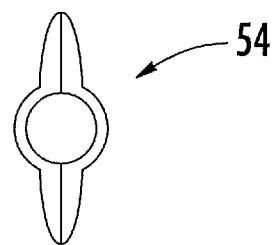
Figure 12D:
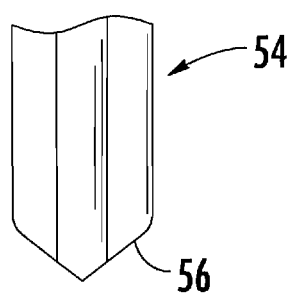

The tube retractor technique starts with identifying the correct entry point, and correct trajectory from the skin to the pathology to be addressed. A top view of the incision 42 is shown in FIG. 10B. The initial soft tissue canulated dilator of circular cross section, as shown in FIG. 12A, is inserted through the incision and forcefully advanced to the objective site. A series of larger diameter dilators as shown in FIG. 12B, 51 and 52, are inserted over the initial dilator sequentially increasing in diameter until the final operative diameter is inserted. The final operative dilator 54 is oblong in cross section as is shown in FIG. 12C through 12F. FIG. 12C is a front perspective view of the ovoid shaped final dilator. FIG. 12D is a side view of the bottom or distal end surface 56 of the final dilator that is convex in shape on both side wall portions. FIG. 12E is a perspective bottom view of the bottom or distal end surfaces of the final dilator that shows the front and back wall surfaces having bottom edges 58 that are concave in shape. The two convex surfaces at the lower edge of the side wall portions and the concave edges on the front and back walls form a distal or end surface that is anatomical in shape and particularly configured to significantly improved the ability to mobilize, dissect, split and retract the terminal tissues of the psoas muscle at the point on the spine where the entry is to be made. Once in its proper position the oblong operative dilator 54 is rotated ninety degrees and then counter rotated back to its original position using the tool 30. FIG. 13 is a top view of the retractor in position on the patient. FIG. 14A is a top view of the retractor 1 in position within the patient's body and FIG. 14B is a side view of the retractor within the patient's body 41. As shown in FIGS. 14A and 14B the spinal disc 60 is located between vertebral bodies 62 and 64. As shown, each vertebral body includes a spinous process bone 66 and a pair of pedicle bones 68. Either segment 6A or 6B can be seen in this view. Once in this position, the retractor 1 is then rotated ninety degrees using tool 30 to the position shown in FIG. 15. FIG. 15 is a top view of the retractor 1 in position on the patient after being rotated. The shape of the distal end of the retractor segments provides a significant improvement in the ability to mobilize, dissect, split and retract the terminal tissues of the psoas muscle at the point on the spine where entry is to be made. Current designs are parallel to the spine and do not comply with the natural shape of the spine, thereby allowing the terminal psoas muscle fibers to creep under the retractor and completely undermine the process and in many cases reduces the overall success and intention of the minimally invasive technique. The ninety degree rotation of the retractor 1 enables the distal portions of the psoas muscle to be mobilized and retracted via the retractor. This action reduces muscle creep thereby reducing the necessity for the surgeon to cut, cauterize and remove muscle fibers to access to the pathology.

Figure 17A:
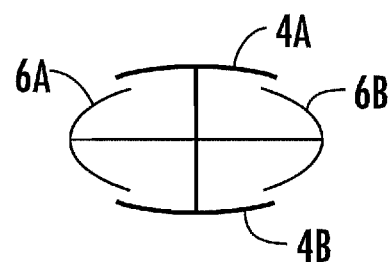
FIGS. 17A and 17B diagrammatically show the spatial relationship between the retractor segments, with FIG. 17B showing the expanded condition.
Figure 17B:
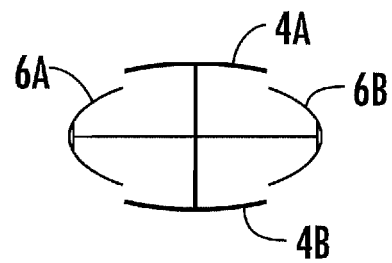
Figure 18A:
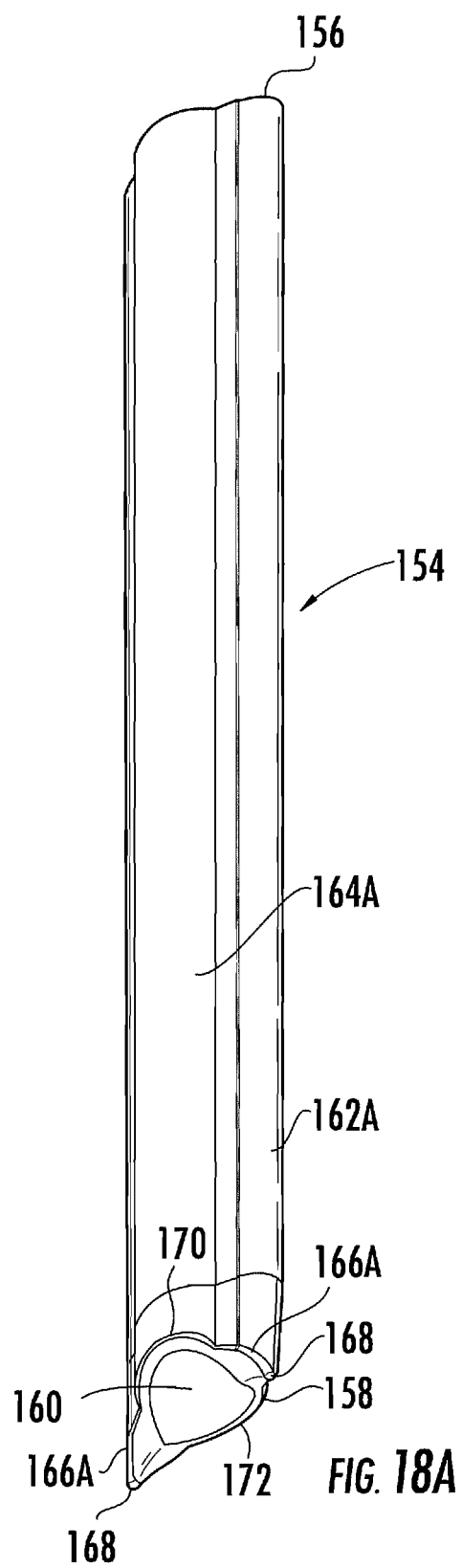
FIG. 18A, is a perspective view of an alternative oblong final dilator.
Figure 18B:
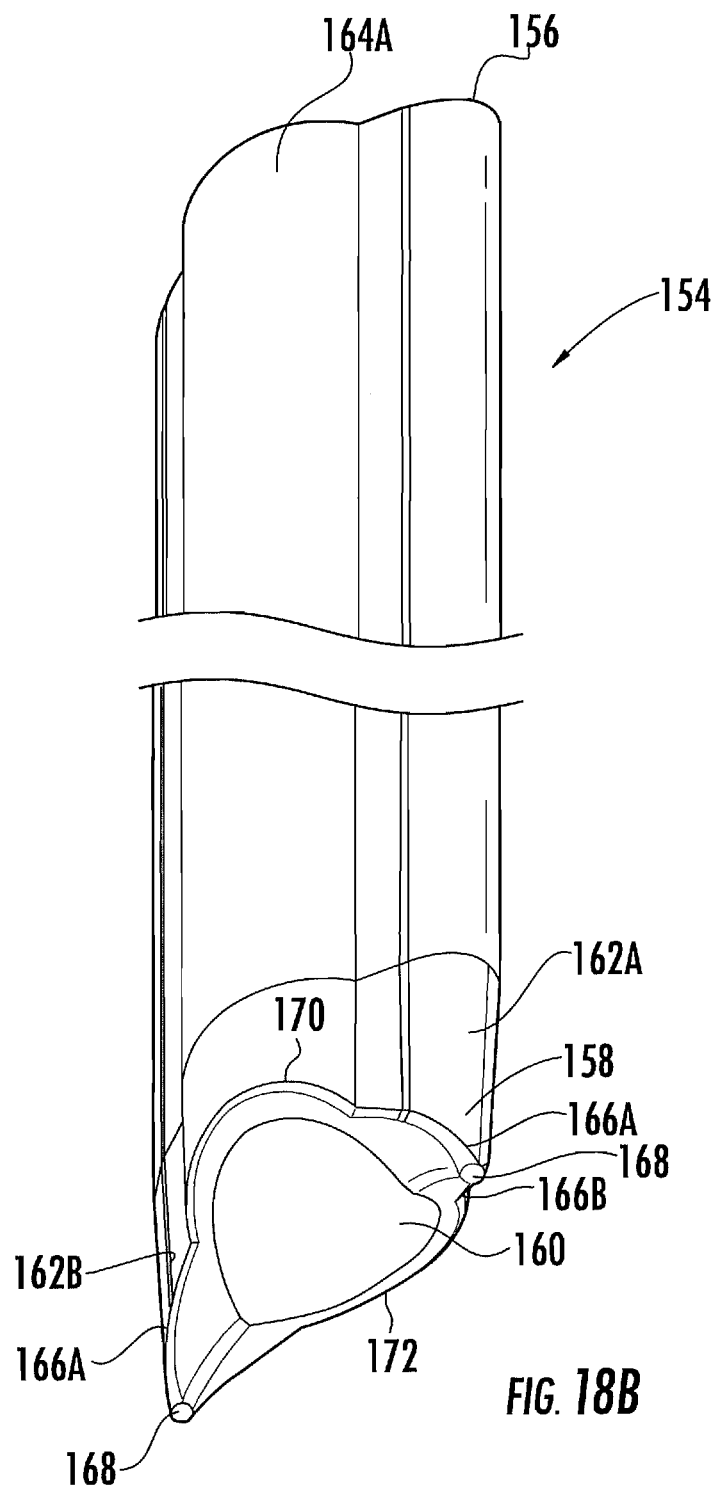
FIG. 18B is a perspective view of the distal end of the final dilator of FIG. 18A.
Figure 18C:
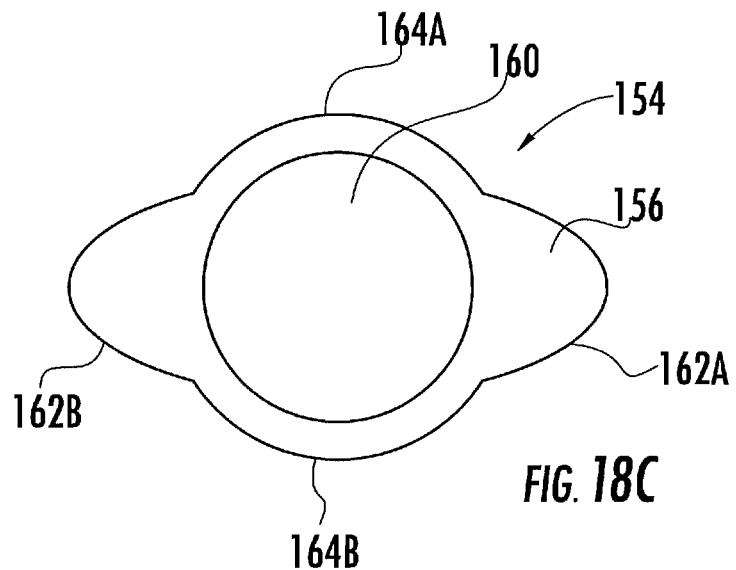
FIG. 18C is a top view of the final dilator shown in FIG. 18A
Figure 18D:
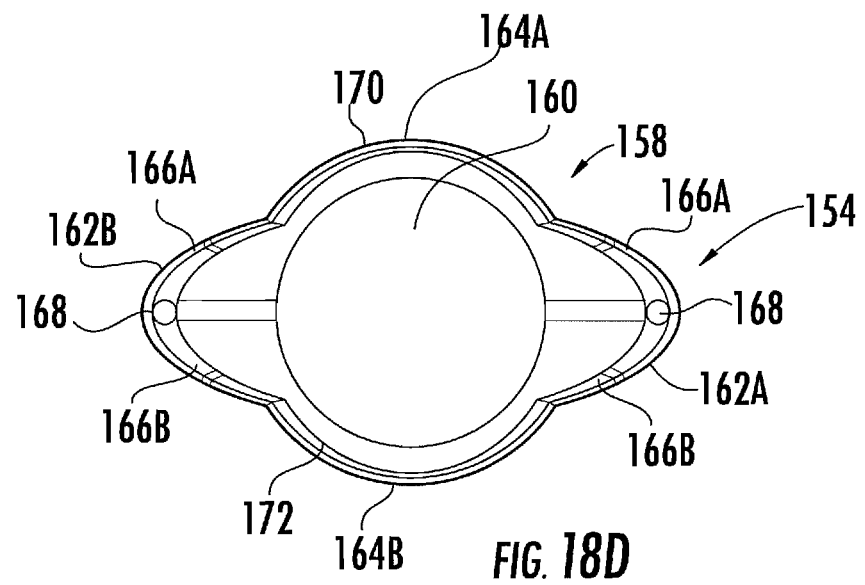
FIG. 18D is a bottom view of the final dilator shown in FIG. 18A.
Figure 19A:
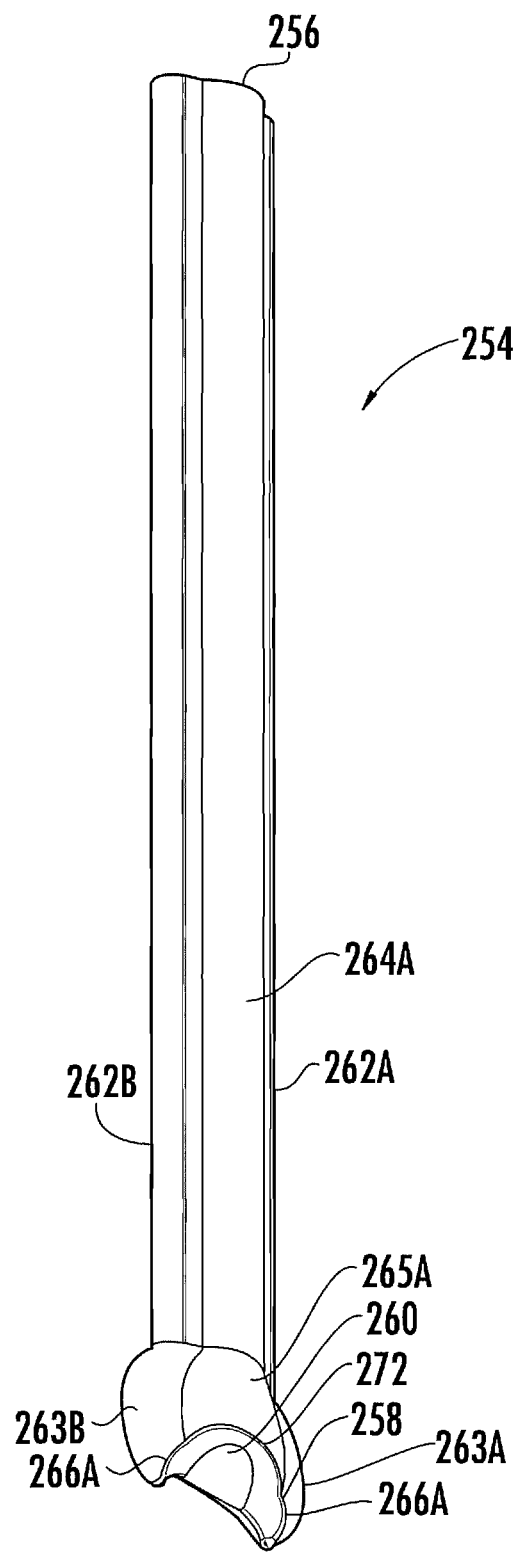
FIG. 19A is a perspective view of another alternative embodiment for the oblong final operative dilator.
Figure 19B:
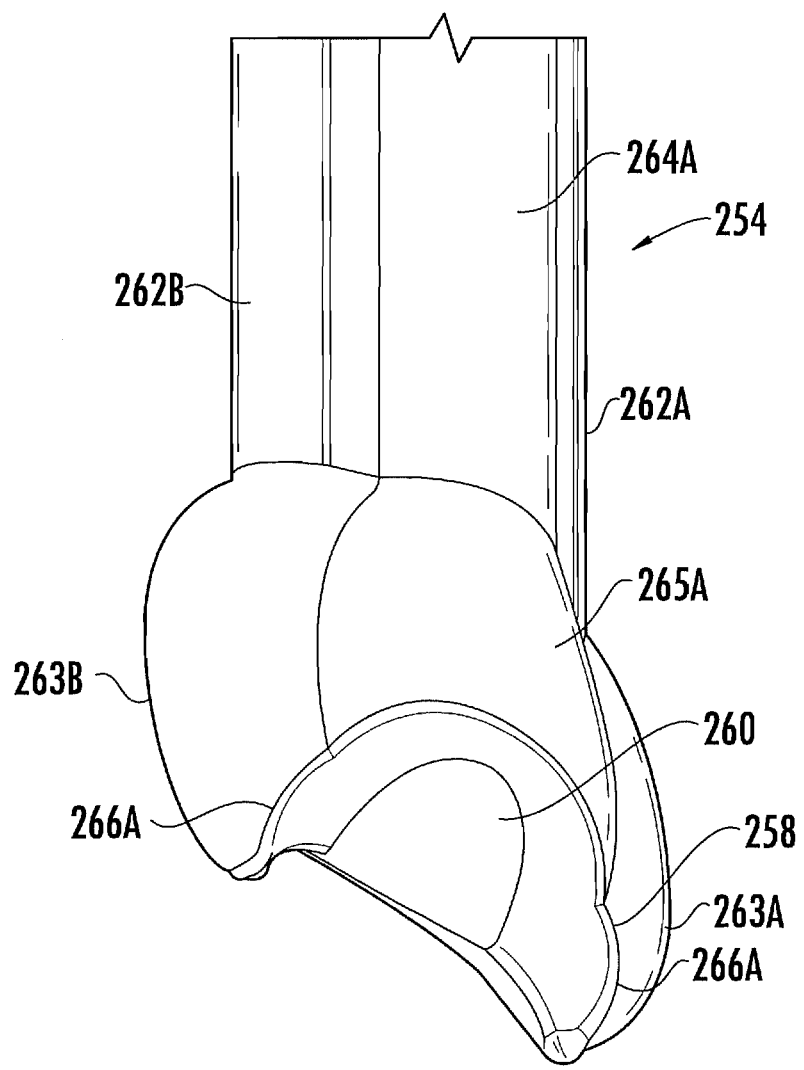
FIG. 19B is a perspective view of the distal end of the final operative dilator shown in FIG. 19A.
Figure 19C:
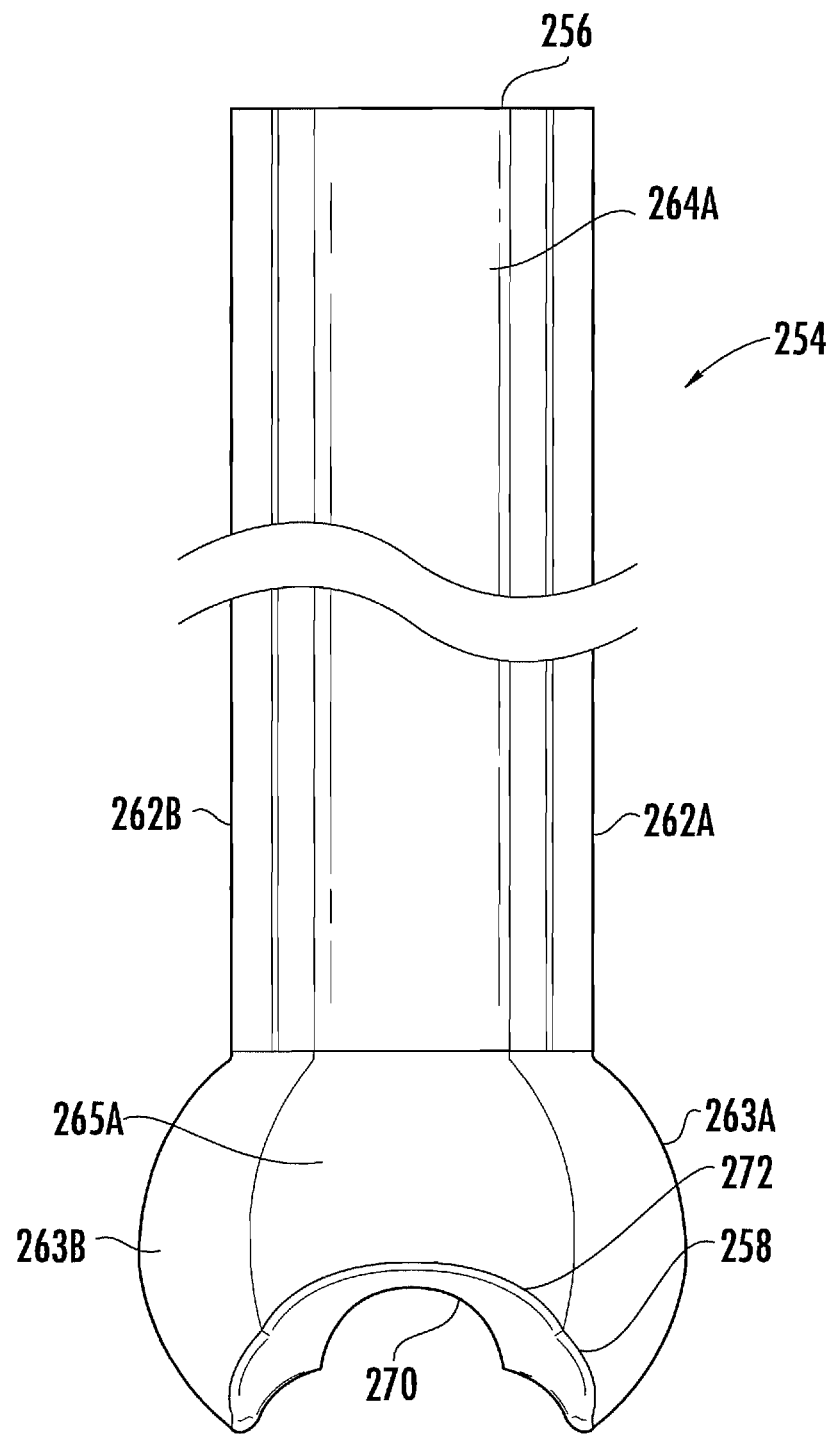
FIG. 19C is a perspective side view of the final operative dilator shown in FIG. 19A.
Figure 19D:
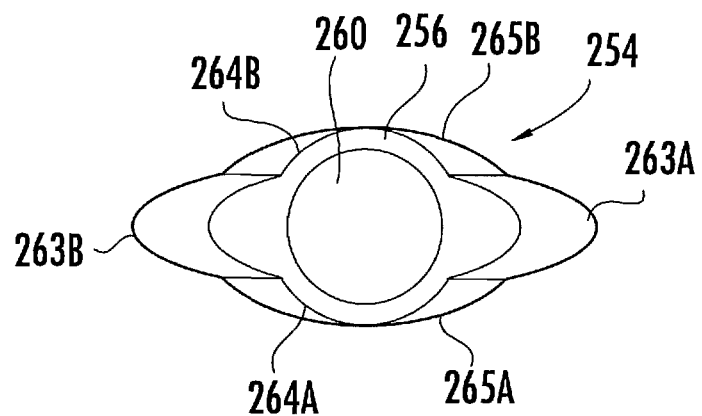
FIG. 19D is a top view of the final operative dilator shown in FIG. 19A.
Figure 19E:
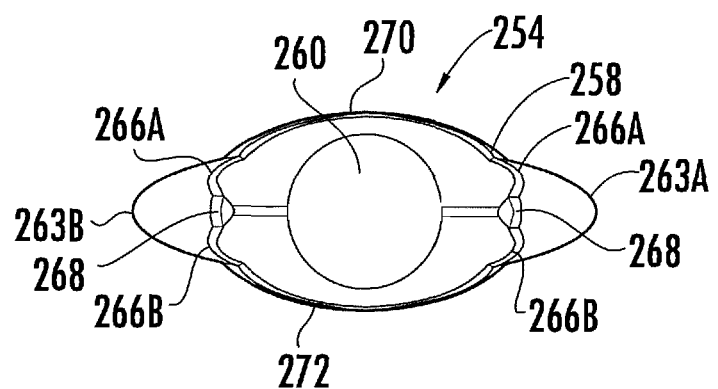
FIG. 19E is a bottom view of the final operative dilator shown in FIG. 19A.

Once the retractor 1 is rotated into final position the final and initial dilators are withdrawn from the patient. At this point, a series of retractor expansion dilators, shown in FIG. 12C, are available for expansion of the retractor 1. These expansion dilators are canulated and assist in centering the retractor with the initial k-wire that is already in place. The expansion dilators are 14, 16, 18 and 20 mm in diameter. As progressively larger expansion dilators are inserted within the retractor 1, segments 4A, 4B, 6A and 6B move relative to one another by virtue of ratcheting mechanisms 8A, 8B, 8C and 8D. By way of example, it is contemplated that the distance between segments 4A and 4B at their mid points can be increased from 14 mm to 18 mm and the distance between segments 6A and 6B at their mid points can be increased from 18 mm to 22 mm, as shown diagrammatically in FIGS. 17A and 17B. At this point the expansion dilators are removed and the operation can proceed. The retractor is anchored at the near portion by frictional engagement with pad 40. In addition the retractor 1 may be anchored at the distal end portion using bone screws that are inserted through holes 12A and 12B of the retractor and threaded into the vertebral body. The pad 40 eliminates the need for a rigid fixation to a point outside the surgical field or to an independent fixed point such as a bed rail. The elimination of these metallic supports that are typically associated with minimally invasive tube or split blade retractors increases the visualization of the approach through the retractor and visualization of the surgical site while using operative fluoroscopy.

The retractor system of the present invention was developed to provide minimally invasive access to a patient's pathology. The ability to dilate muscle tissue, as opposed to the process where the muscle tissue is stripped or detached from the skeletal structure will usually reduce the morbidity associated with the standard invasive technique. The procedure utilizing the retractor system of the present invention starts with the identification of the correct entry point, the proper trajectory from the skin to the pathology to be addressed as well as the point of incision. After the initial incision has been made through the patient based anchoring pad and into the skin the initial soft tissue dilator is inserted through the incision and forcefully advanced to the objective site. The initial dilator is 6 mm in diameter and round in cross section. Thereafter, a series of progressively larger dilators are inserted over the initial dilator; increasing in diameter until the final operative dilator is inserted. The final operative dilator is oblong in cross section. Once the final operative oblong dilator is in place it is then rotated ninety degrees by tool 30 and then counter rotated ninety degrees back to its initial position. The retractor 1 is then placed over the final operative dilator and forcefully advanced to the objective site. Once in position the retractor is then rotated ninety degrees by using a tool 30. Thereafter the initial and final dilators are removed. Following removal of the dilators used for initial delivery, a series of expansion dilators, are inserted into the center of the retractor 1 to expand the open area or portal within the retractor. These expansion dilators are circular in cross section and range in diameter from 14 mm to 20 mm. As the expansion dilators are inserted the ratcheting mechanisms 8A, 8B, 8C, and 8D allow relative movement between the adjacent retractor segments by virtue of the disengagement and reengagement of the teeth 20 and 22. The expansion dilator creates a force directed radially outwards thereby causing a shift in the alignment of teeth 20 and 22. Simultaneously resilient sleeve 10 exerts a radially inward directed force maintaining the teeth 20 and 22 in their newly established position.

FIGS. 18A, 18B, 18C and 18D illustrate various views of an alternative embodiment for the oblong final operative dilator. As shown in these views the final operative dilator 154 includes an upper, proximate, edge 156 and a lower, distal, edge 158. The dilator includes a central passageway 160 that is generally cylindrical in cross section and extends the entire length of the dilator 154 from the upper edge 156 to the lower edge 158. The outer surface of the dilator 154 generally conforms to the inner surface of the retractor and includes a pair of opposing semi elliptical surfaces 162A and 162B as well as a second pair of opposing semi elliptical surfaces 164A and 164B which together form a contiguous outer surface of the final operative dilator 154. The upper edge surface 156 is generally planar and formed orthogonally with respect to the outer surface of the retractor. The lower distal edge 158 is formed from a plurality of thin arcuate surfaces forming a concave shape at the distal end of the dilator. The walls of the distal end portion are tapered to form this series of thin arcuate surfaces. The arcuate surfaces includes a pair of curved surfaces 166A and 166B proximate the distal ends of semi elliptical surfaces 162A and 162B. Surfaces 166A and 166B are connected at a point 168 located at the most distal end of the dilator. Formed on the lower distal edge surface 158 adjacent opposing semi elliptical surfaces 164A and 164B are curved surfaces 170 and 172. Each of the curved surfaces 170 and 172 has a first and second ends connected to the curved surfaces 166A and 166B. The mid point of surfaces 170 and 172 being located closer to the upper surface of the final dilator. The lower distal edge 158 thereby forming an anatomically concave shape at the tip of the dilator. The concave shaped distal end extends over the disc/endplate interface. The concave shape will gently divide the muscle and fiber tissue. The anatomically curved distal tip of the dilator gently separates the final psoas fibers directly attached to the interverbral disc/vertebral body interface along the lateral aspect of the spine. This gentle splitting of the fibers occurs along the same plane as the muscle fibers which ensure a split/separation action. By mobilizing a longer axis of muscle fibers the forces normally associated with larger dilators are applied along a greater surface area of tissue which reduces the forces directly associated with the immediate surrounding tissues and of greater consequence, the neural tissues such as the lumber plexus. Once the fibers have been split along the length of the muscle a gentle rotation of the dilator gently sweeps the terminal fibers attached to the lateral aspect of the intervertebral disc. This enables the tissues to be swept and subsequently maintained outside the working area once the retractor is placed and rotated into its final working position. This action will result in a less disruptive means of exposure thereby reducing the need for cutting or electro-cauterizing the final fibers while providing better visualization of the target area of surgery.

Current dilators and retractors use a cylindrical design with a flat planar surface. They rely on compression of the fibers at the distal aspect of the device to achieve dilation. Typically retractors use compressive forces, sequentially, to distract a parallel opening which increases muscle disruption and potential nerve compression. This arrangement allows for the final fibers to creep under the edges of the retractor and does not allow for sweeping of the final fibers. When the typical retractor is opened with the final fibers still intact within the target area for surgery, they will need to be moved with instruments that makes the process, tedious and increases the risk of neural and vascular structures being unintentionally cut or crushed as the fibers and tissue are cut, torn and/or electro cauterized.

FIGS. 19A, 19B, 19C, 19D and 19E illustrate various views of another alternative embodiment for the oblong final operative dilator. As shown in these views the final operative dilator 254 includes an upper, proximate, edge 256 and a lower, distal, edge 258. The dilator includes a central passageway 260 that is generally cylindrical in cross section and extends the entire length of the dilator 254 from the upper edge 256 to the lower edge 258. The outer surface of the dilator 254 includes a pair of opposing semi elliptical surfaces 262A and 262B as well as a second pair of opposing semi elliptical surfaces 264A and 264B which together form a contiguous outer surface of the final operative dilator 254. The distal end of dilator 254 includes concave outer surfaces that extend outwards in a curved fashion from the semi elliptical surfaces 262A, 262B, 264A and 264B. Concave surface 263A extends radially outward from surface 262A. Concave surface 263B extends radially outward from surface 262B. Concave surface 265A extends radially outward from surface 264A and concave surface 265B extends radially outward from surface and 265A. The upper edge surface 256 is generally planar and formed orthogonally with respect to the outer surface of the dilator. The lower distal edge 258 is formed from a plurality of thin arcuate surfaces forming a concave shape at the distal end of the dilator. The walls of the distal end portion are tapered to form this series of thin arcuate surfaces. The arcuate surfaces includes a pair of curved surfaces 266A and 266B proximate the distal ends of semi elliptical surfaces 262A and 262B. Surfaces 266A and 266B are connected at a point 268 located at the most distal end of the dilator. Formed on the lower distal edge surface 258 adjacent opposing semi elliptical surfaces 264A and 264B are curved surfaces 270 and 272. Each of the curved surfaces 270 and 272 has a first and second ends connected to the curved surfaces 266A and 266B. The mid point of surfaces 270 and 272 being located closer to the upper surface of the final dilator. The lower distal edge 258 thereby forming an anatomically concave shape at the tip of the dilator. The concave shaped distal end extends over the disc/endplate interface. As final operative dilator 254 has a distal end that includes concave outer surfaces that extend outwards in a curved fashion from the semi elliptical surfaces 262A, 262B, 264A and 264B it will be removed from the incision after its insertion and the aforementioned rotation prior to insertion of the retractor. The configuration of the final operative dilator 254 will split the psoas muscle in the same manner as described with respect to final operative dilator 154.

Figure 20:
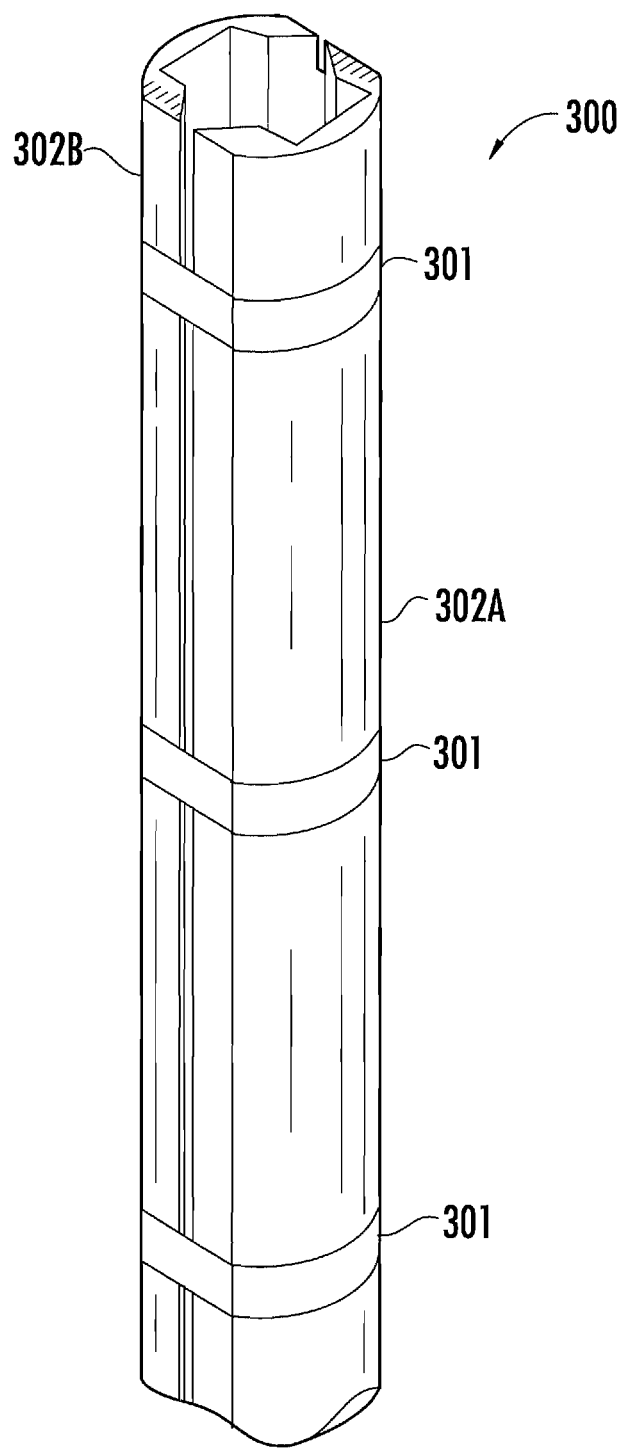
FIG. 20 is a perspective view of an alternative embodiment of the adjustable retractor.

FIG. 20 is a perspective view of an alternative embodiment of the adjustable retractor 300. Retractor 300 is an elongated body that is made up of a plurality of selectively engaging segments. The segments include a first pair of elongated members 302A and 302B having opposed semi elliptical shaped cross section and a second pair of elongated members 304A and 304B having opposed semi elliptical shaped cross section. Each segments has a top, or proximate, portion and a bottom, or distal, portion. The length of the elongated members being of a length to span the distance from adjacent the surgical area at the distal end portion to a location external to the patient. The distal end of the retractor 300, comprised of the distal ends of elongated members 302A, 302B, 304A and 304B, has the correct concave shape to allow for more effective dissection of the terminal tissues at the distal end of the retractor 300.

Figure 21:
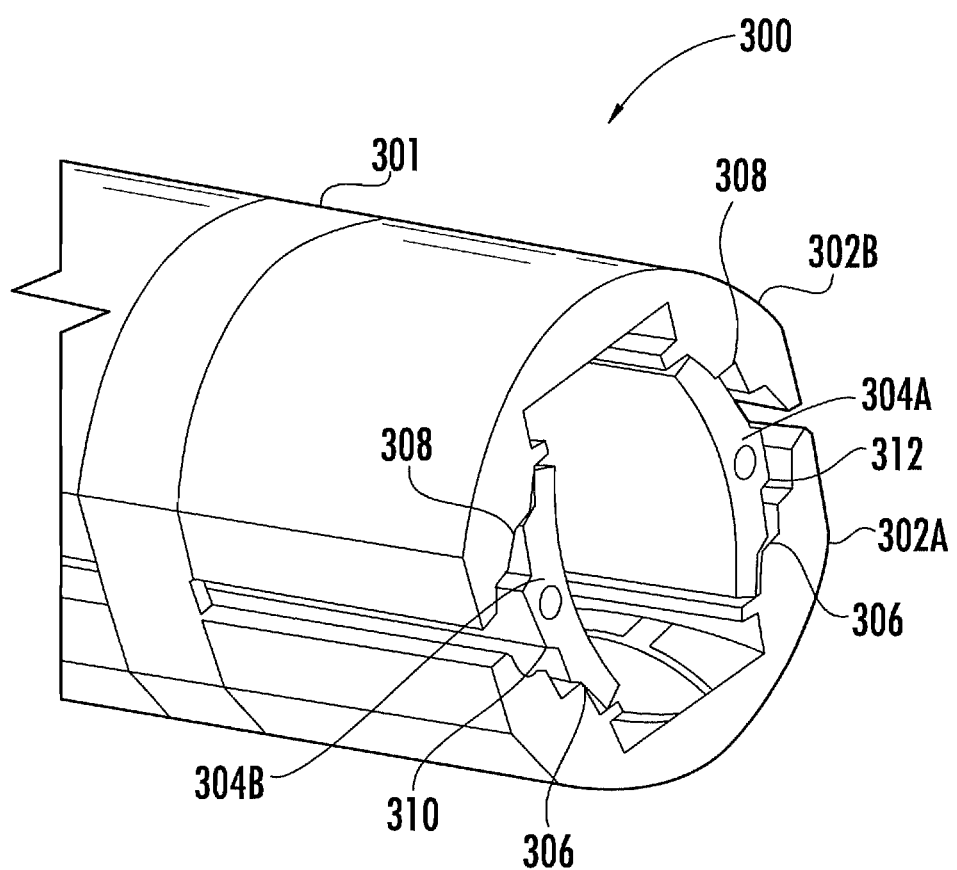
FIG. 21 is a top view of the retractor shown in FIG. 20 with the retractor in its most compact configuration

FIG. 21 is a top view of the retractor shown in FIG. 20 with the retractor in its most compact configuration. As can be seen in this view, elongated members 302A and 3023 have step like teeth 306 and 308 that are directed radially inward while elongated members 304A and 304B have complimentary teeth 310 and 312 that are directed radially outward. Teeth 306 and 308 on members 302A and 302B and teeth 310 and 312 on members 304A and 304B generally run the length of the retractor from the proximate to the distal end. The elongated members are retained in a fixed position under the influence of elastomeric bands 301 that exert a radially directed inward force. Three elastomeric bands are shown in FIG. 20, by way of example, recognizing that more than three or less than three can be used as well. The elastic bands provide the tension necessary to maintain multiple pieces together during initial insertion of the dilator. They also provide the appropriate amount of tension required to allow sequential dilation/opening of the retractor in parallel fashion along the length of the retractor. This aspect of the invention eliminates a problem associated with current retractors wherein the application of dilating force at the proximal end to overcome the physiological forces applied to the human anatomy at the distal end results in a larger opening proximally with little effect and a smaller opening distally. This problem runs counter to the overall objective of minimally invasive proximal openings with minimal disruption of the terminal fibers at the intended surgery target area.

Figure 22:
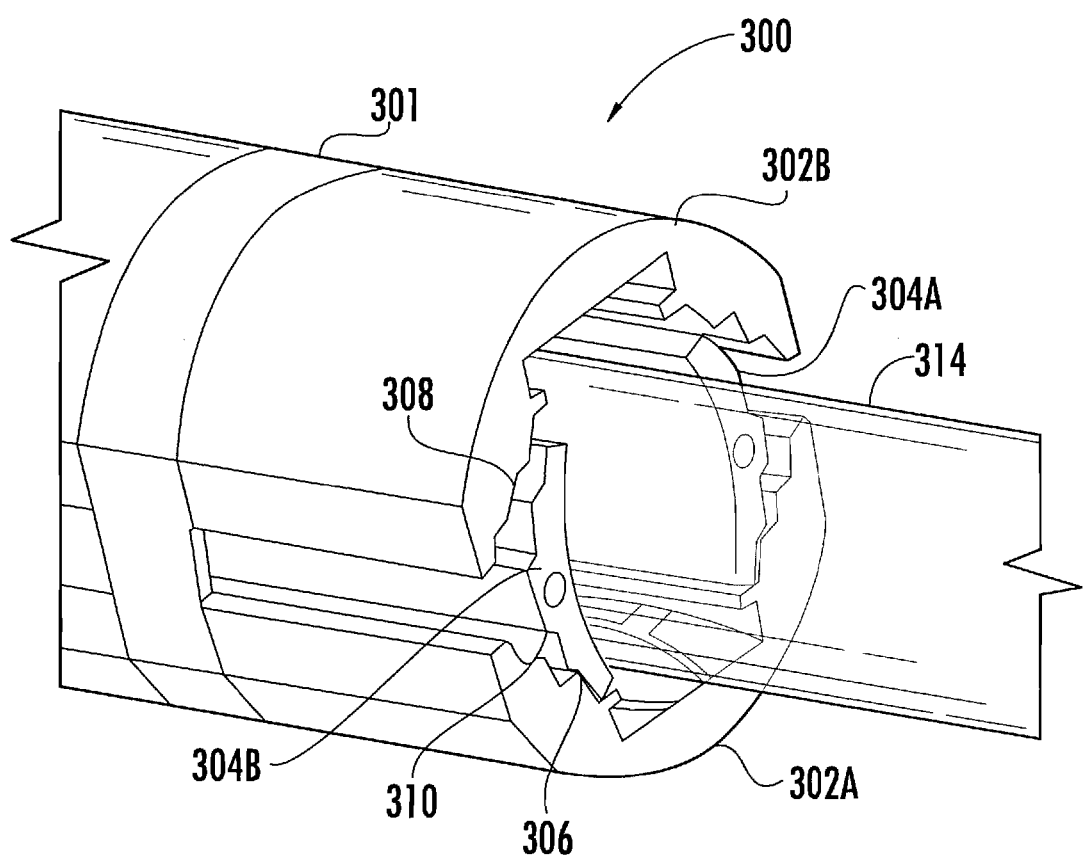
FIG. 22 is a top view of the retractor shown in FIG. with a retractor dilator expanding the retractor an intermediate expanded configuration.
Figure 23A:
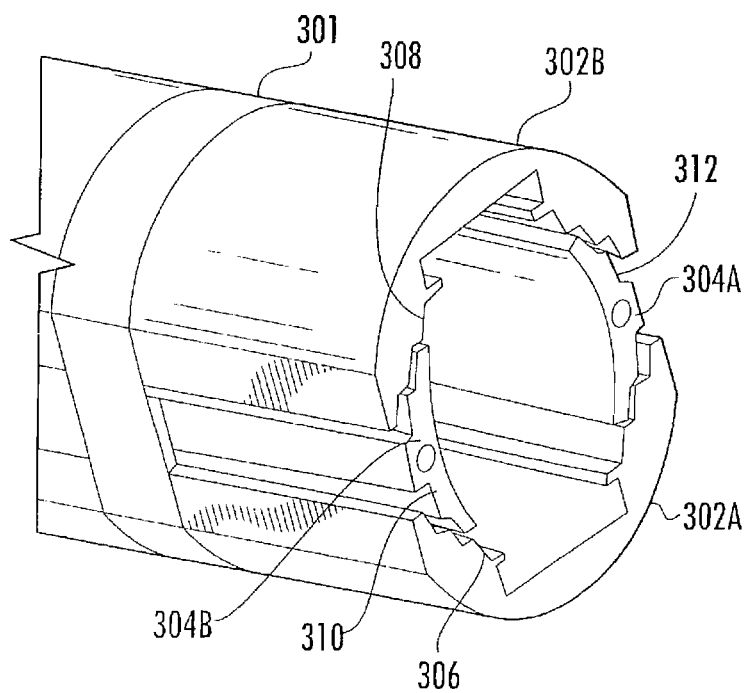
FIG. 23A is a top view of the retractor shown in FIG. 20 with the retractor in an intermediate position between most compact and most expanded configuration.

FIG. 22 is a top view of the retractor shown in FIG. 20 with a retractor dilator expanding the retractor an intermediate expanded configuration. As can be seen in this view, as a first retractor dilator 314 is inserted into a cavity formed within the assembly of elongated members 302A and 302B are urged radially apart from one another thereby disengaging the step like teeth on the elongated members. At the same time the first retractor dilator 314 urges the elongated members 310 and 312 radially outward. Upon removal of the first retractor dilator 314 the retractor 300 has been reconfigured to an intermediate position as shown in FIG. 23A wherein the elongated members 310 and 312 have moved radially outward to the next step on elongated members 302A and 302B. Upon removal of the retractor dilator the elastomeric bands 301 will again exert a radially directed inward force and maintain engagement of the teeth on the elongated members, as shown in FIG. 23A.

Figure 23B:
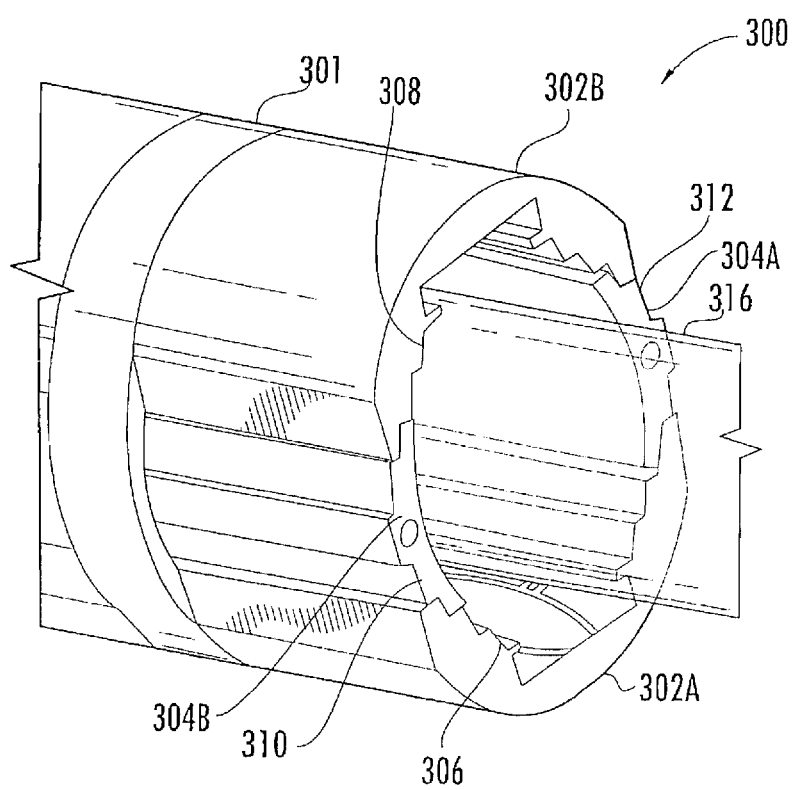
FIG. 23B is a top view of the retractor of FIG. 20 with a retractor dilator urging the retractor to the most expanded configuration.

FIG. 23B is a top view of the retractor of FIG. 20 with a second retractor dilator urging the retractor to the most expanded configuration. The second retractor dilator 316 is larger than the first retractor dilator 314. As the second retractor dilator 316 is inserted into a cavity formed within the assembly of elongated members, members 302A and 302B are urged radially apart from one another thereby disengaging the step like teeth on the elongated members. At the same time the second retractor dilator 316 urges the elongated members 310 and 312 radially outward. Upon removal of the second retractor dilator 316 the retractor 300 has been reconfigured to a final position as shown in FIG. 23B wherein the elongated members 310 and 312 have moved radially outward to the next step on elongated members 302A and 302B. The elastomeric bands 301 will again exert a radially directed inward force and maintain engagement of the teeth on the elongated members, as shown in FIG. 23B.

Figure 24A:
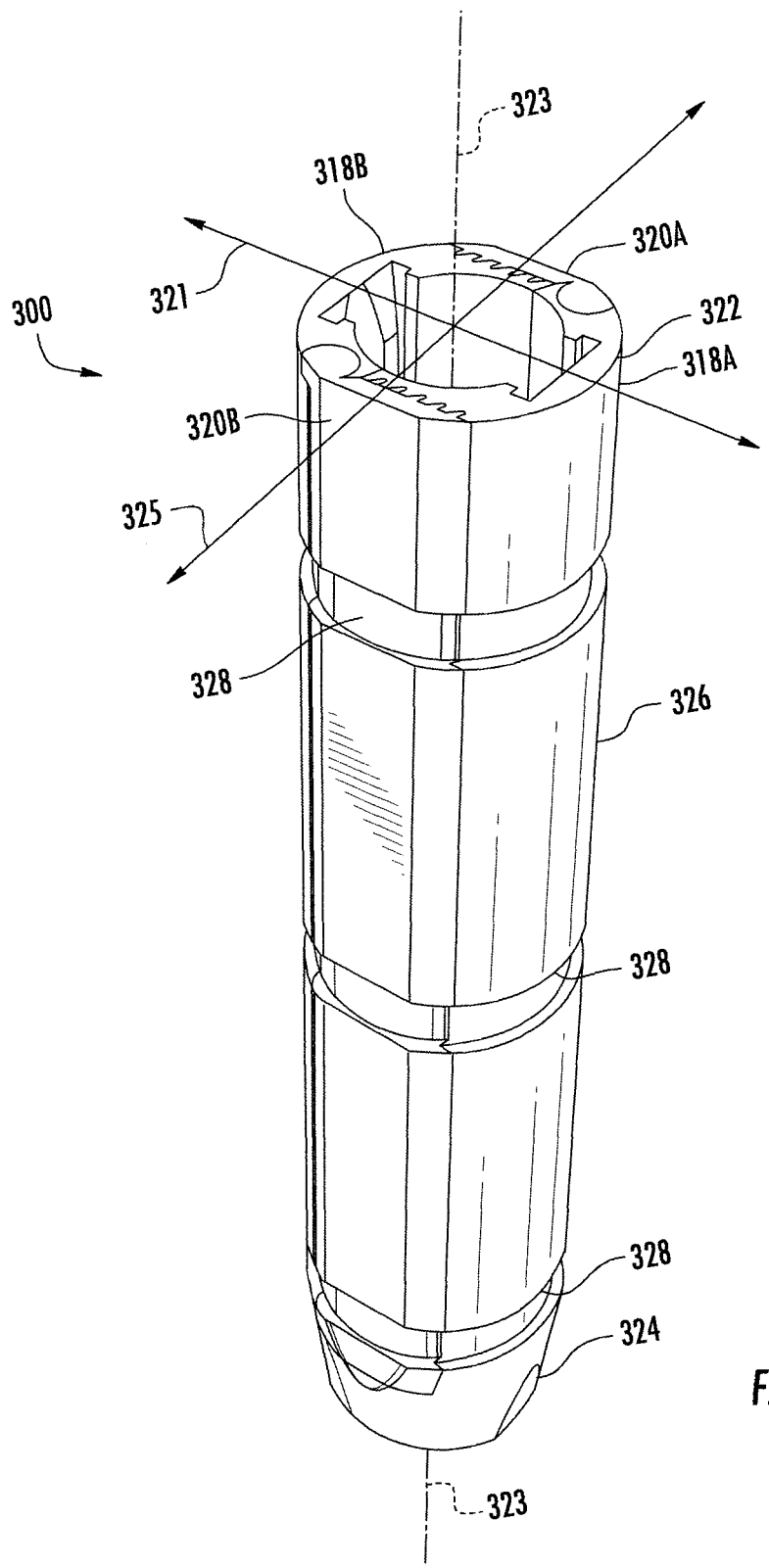
FIG. 24A a perspective view of an alternative embodiment of the adjustable retractor.

FIG. 24A is a perspective view of an alternative embodiment of the adjustable retractor 300. Similar to the retractor shown in FIGS. 20-23B, the retractor 300 illustrated in FIG. 24A is an elongated body comprising a plurality of engaging segments. The segments may include, for example, a first pair of elongated members 318A and 318B having opposed semi elliptical shaped cross section and a second pair of elongated members 320A and 320B having opposed semi elliptical or semi cylindrical shaped cross section. Each of the segments has a top, or proximate, portion (forming the proximate end portion of the retractor 322, and a bottom, or distal, portion (forming the dial end portion 324 of the retractor 300). In a particular embodiment, the elongated members 318A and 318B are arranged oppositely about a first plane 321 formed substantially perpendicular to a longitudinal axis 323 and the second pair of elongated members 320A and 320B are arranged oppositely about a second plane 325, the second plane 325 having a different orientation about the longitudinal axis 323 than the first plane 321. That orientation could be, for example, 90 degrees, less than 90 degrees, or greater than 90 degrees.

The length of the elongated members preferably being a length to span the distance from adjacent the surgical area at the distal end portion to a location external to the patient. The distal end 324 of the retractor 300, comprised of the distal ends of the elongated members 318A, 318B, 320A, and 320B may be shaped, for example containing a correct concave shape, to allow for more effective dissection of the terminal tissues at the distal end of the retractor. When all four elongated members 318A, 318B, 320A, and 320B are configured together, the body 326 of retractor 300 contains one or more spaced apart recessed channels 328 sized and shaped to receive and hold elastic member such as band 301 as described previously. The elongated members 318A, 318B, 320A, and 320B are retained in a fixed position under the influence of elastomeric bands 301 that exert a radially directed inward force. Three recessed channels 328 are shown in FIG. 24A, by way of example, recognizing that more than three or less than three can be used as well. The elastic bands provide the tension necessary to maintain multiple pieces together during initial insertion of the dilator. They also provide the appropriate amount of tension required to allow sequential dilation/opening of the retractor in parallel fashion along the length of the retractor.

Figure 24B:
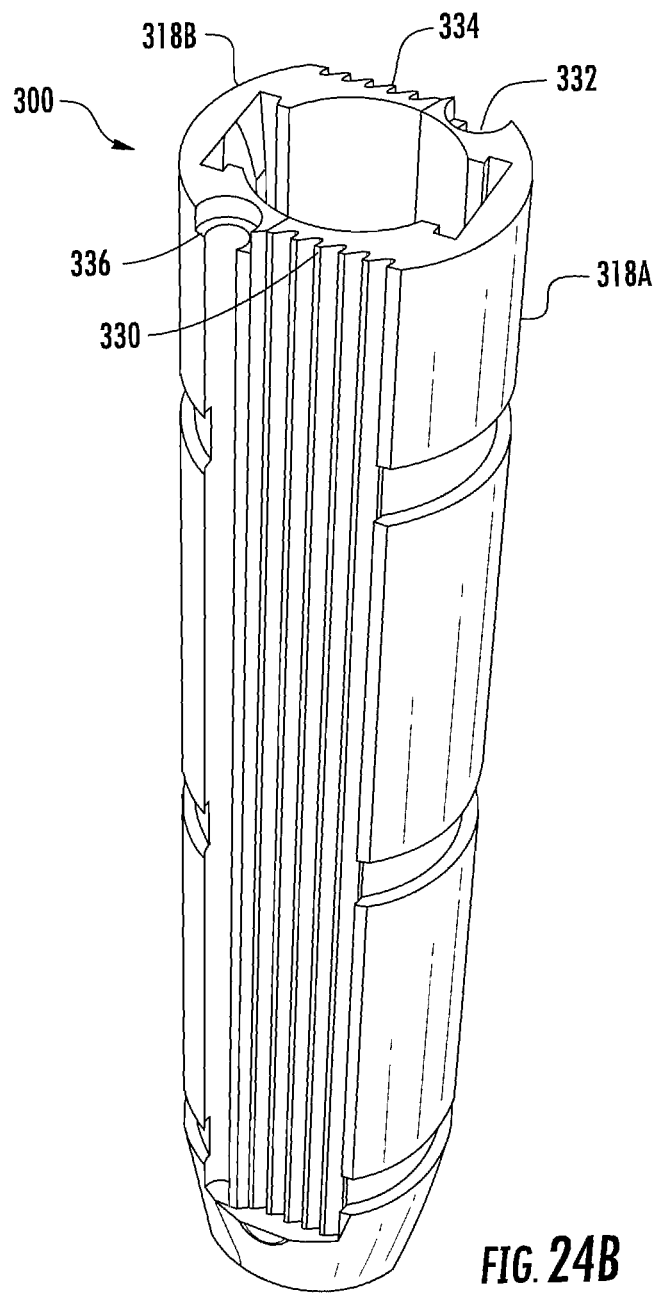
FIG. 24B is a perspective view of the adjustable retractor illustrated in FIG. 24A shown with the second pair of elongated members removed.
Figure 24C:
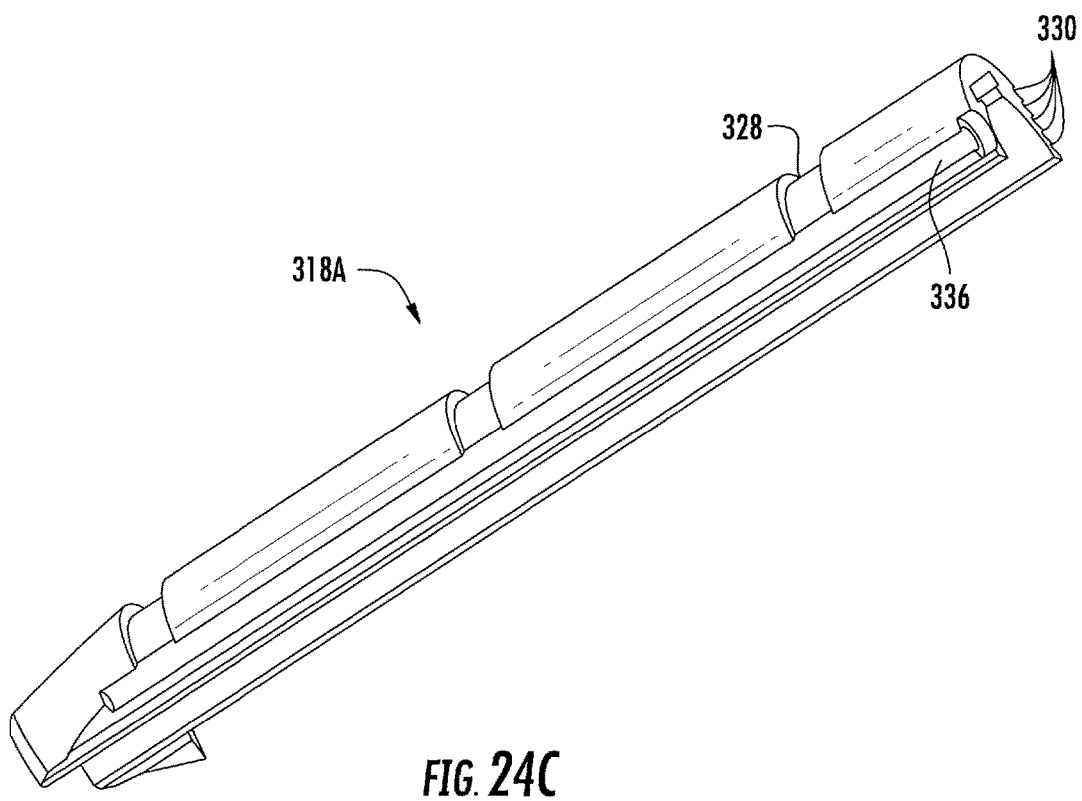
FIG. 24C is a perspective view of an elongated member of the first pair of elongated members.

FIG. 24B shows the retractor 300 illustrated in FIG. 24B without the elongated members 320A and 320B. One side of the elongated member 318A contains a plurality of stepped surfaces 330 forming to form engaging teeth. Opposing the stepped surfaces 330 is a semicircular recessed region 332, see also FIG. 24C. The semicircular recessed region 332 is preferably begins at or near the proximate portion 322 of the retractor, running the length of the elongated member 318A, and terminating at or near the distal end portion 328. Elongated member 318B contains a similar structure as that described for elongated member 318A. Elongated member 318B contains a plurality of stepped surfaces 334 forming to form as second set of engaging teeth. Opposing the stepped surfaces 333 is a second semicircular recessed region 336. The semicircular recessed region 336 preferably begins at or near the proximate portion 322 of the retractor, running the length of the elongated member 318B, and terminating at or near the distal end portion 328.

Figure 24D:
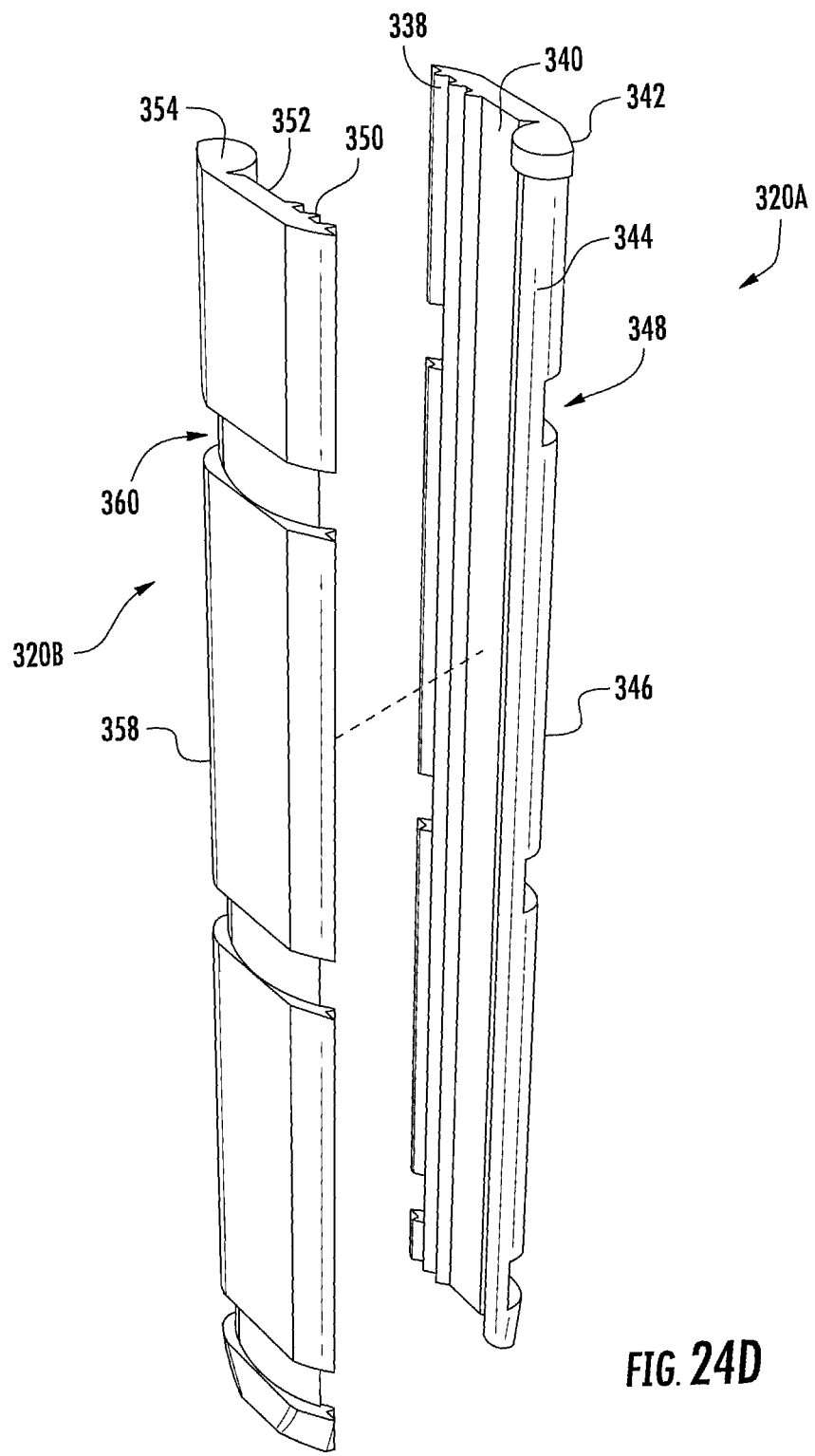
FIG. 24D is a perspective view of the second pair of elongated members.
Figure 24E:
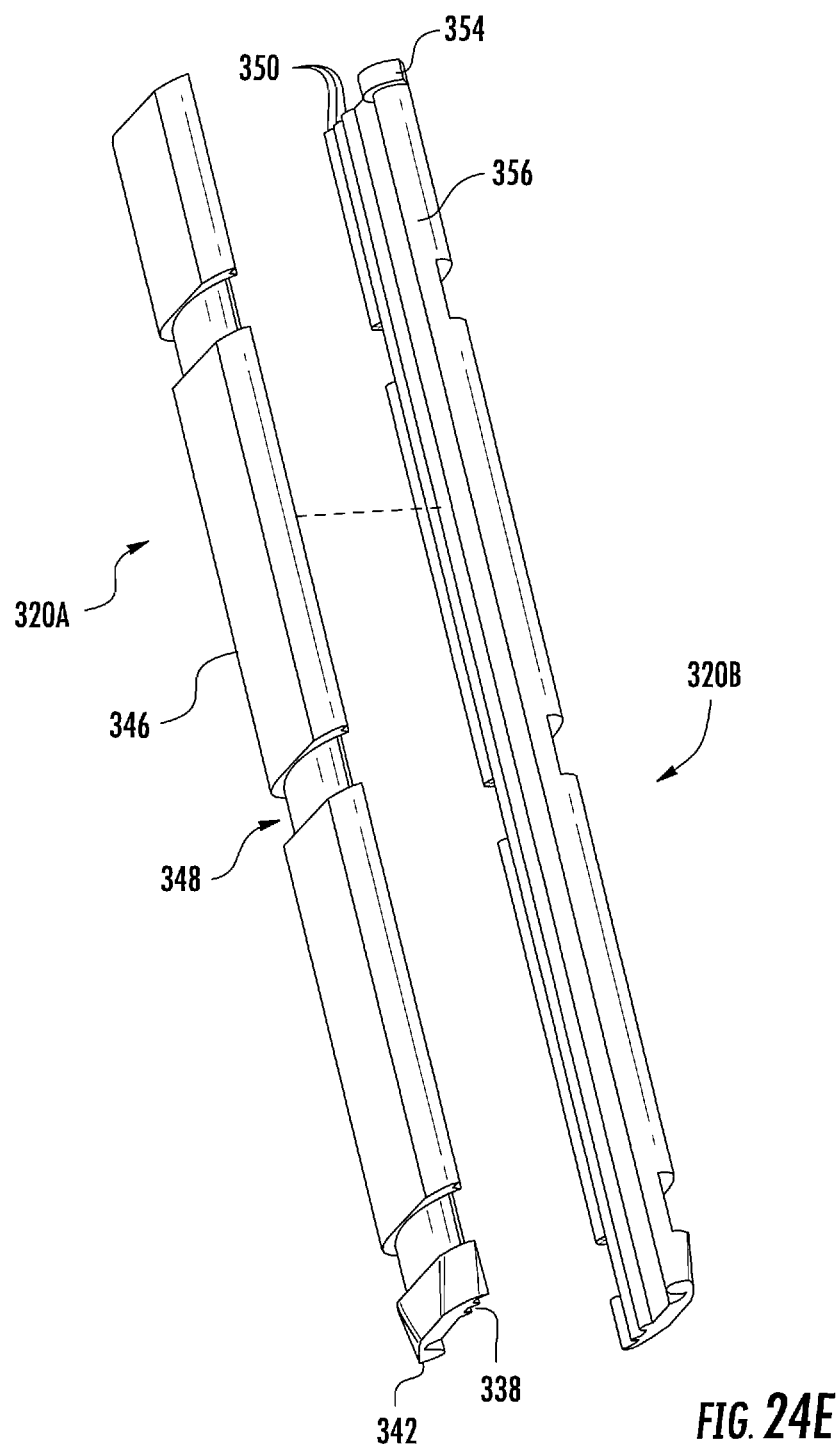
FIG. 24E is an alternative view of the second pair of elongated members shown in FIG. 24D.

FIG. 24D and FIG. 24E show illustrative embodiments of elongated members 320A and 320B. The elongated member 320A contains a first portion having stepped surfaces 338 positioned within an inner surface 340. The stepped surfaces 338 preferably extend the length of the elongated member 320A. Positioned at the opposite end of the stepped surfaces 338 is a partially cylindrical member 342. The partially cylindrical member 342 protrudes away from the inner surface 340 and has a body 344 which spans the length of the elongated member 320A and is sized and shaped to fit within and engage with the semicircular recessed region 332 of elongated member 318A. Engagement of the partially cylindrical member 342 with the semicircular recessed region 332 of elongated member 318A forms a hinged connection.

The stepped surfaces 338 are sized and shaped to engage with the plurality of stepped surfaces 334 of elongated ember 318B. Accordingly, the stepped surfaces 338 and the elongated ember 318B cooperate in an interdigiting fashion to restrain lateral contracting of the elongated ember 318B with respect to the elongated member 320A. However, the plurality of stepped surfaces 334 and the stepped surfaces 338 yield sufficiently to allow lateral expansion of the contractor 300. This arrangement allows for the elongated member 320A to: 1) hingedly engage with a portion of one elongate member, and 2) expandably engage, via interdigiting cooperation, with a second, independent elongated member. The outer surface 346 contains a plurality of recessed regions 348 which when assembled form part of the channel 328 of the retractor 300.

Elongated member 320B contains a first portion having stepped surfaces 350 extending from an inner surface 352. The stepped surfaces 350 preferably extend the length of the elongated member 320B. Positioned at the opposite end of the stepped surfaces 350 is a partially cylindrical member 354. The partially cylindrical member 354 protrudes away from the inner surface 352 and has a body 356 which spans the length of the elongated member 320B. The partially cylindrical member 354 is sized and shaped to fit within and engage with the semicircular recessed region 336 of elongated member 318B. Engagement of the partially cylindrical member 354 with the semicircular recessed region 336 of the elongated member 318B forms a hinged connection.

The stepped surfaces 350 are sized and shaped to engage with the plurality of stepped surfaces 330 of the elongated member 318A. Accordingly, the stepped surfaces 330 and the elongated ember 318A cooperate in an interdigiting fashion to restrain lateral contracting of the elongated ember 318A with respect to the elongated member 320B. However, the plurality of stepped surfaces 330 and the stepped surfaces 350 yield sufficiently to allow lateral expansion of the contractor 300. This arrangement allows for the elongated member 320B to: 1) hingedly engage with a portion of one elongate member, and 2) expandably engage, via interdigiting cooperation, with a second, independent elongated member. The outer surface 358 contains a plurality of recessed regions 360 which when assembled form part of the channel 328 of the retractor 300.

Figure 24F:
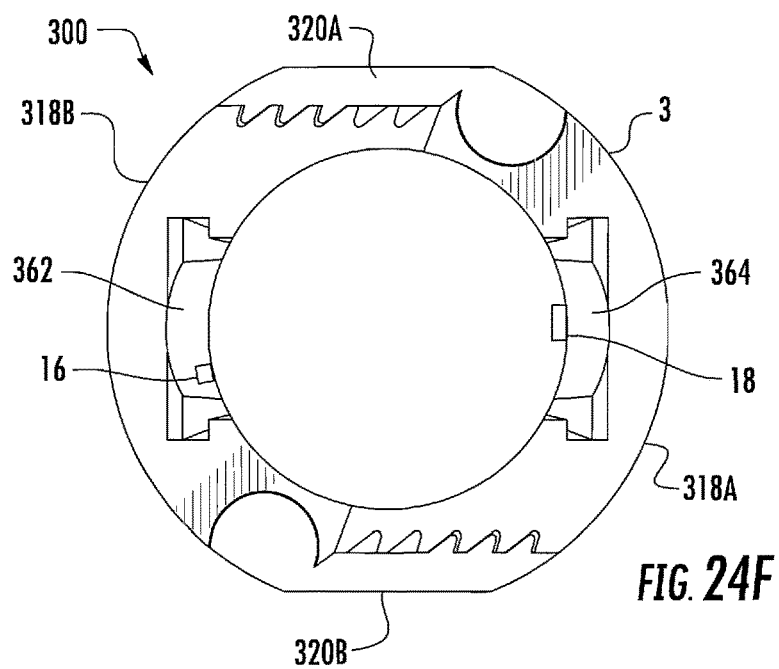
FIG. 24F is a top view of the adjustable retractor illustrated in FIG. 24A.
Figure 24G:
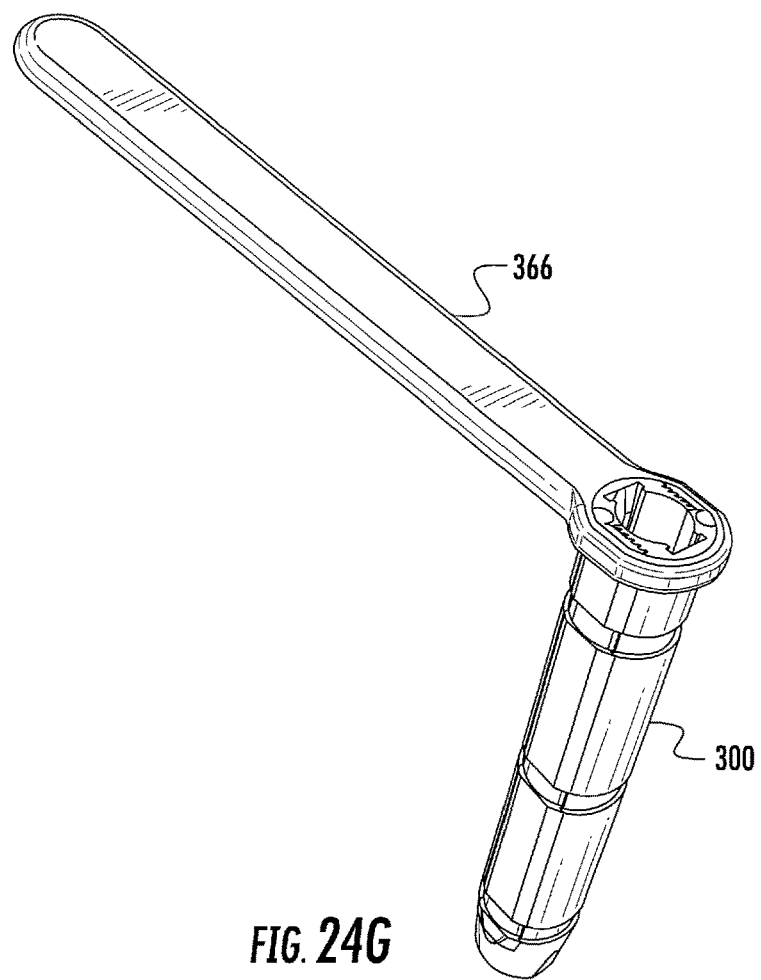
FIG. 24G is a perspective view of the adjustable retractor engaged with a hand tool.
Figure 24H:
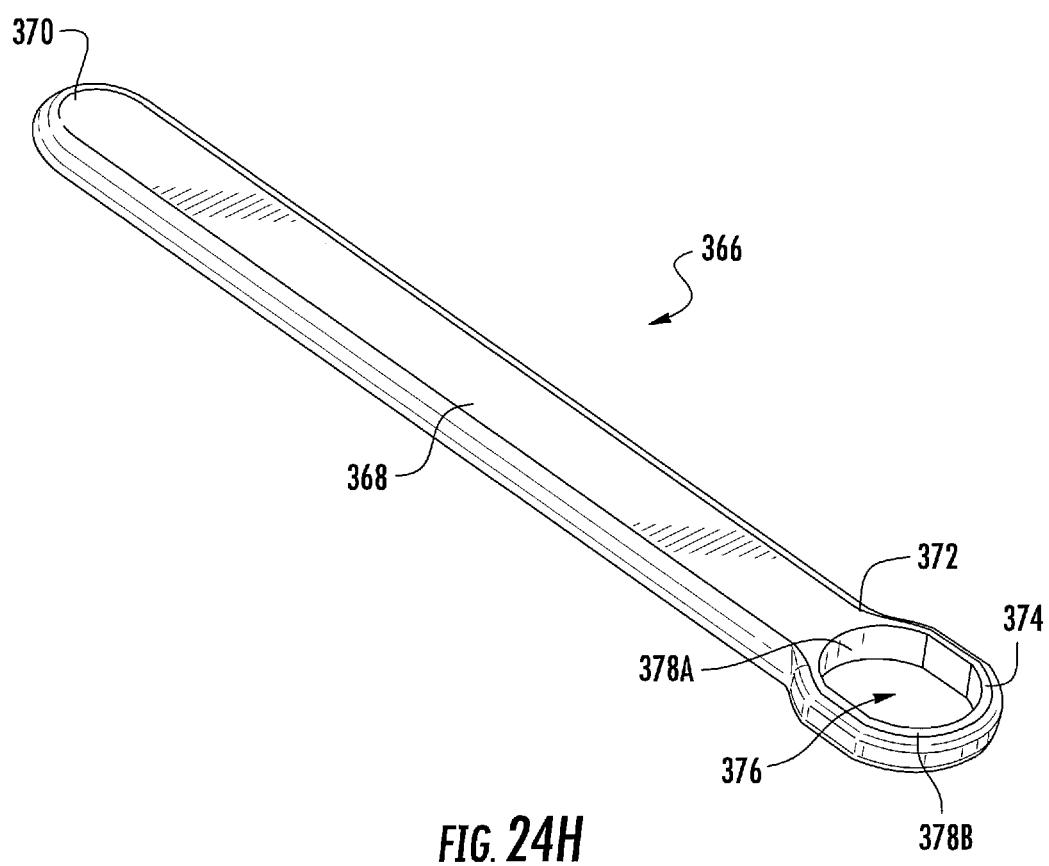
FIG. 24H is a perspective view of the hand tool.
Figure 24I:
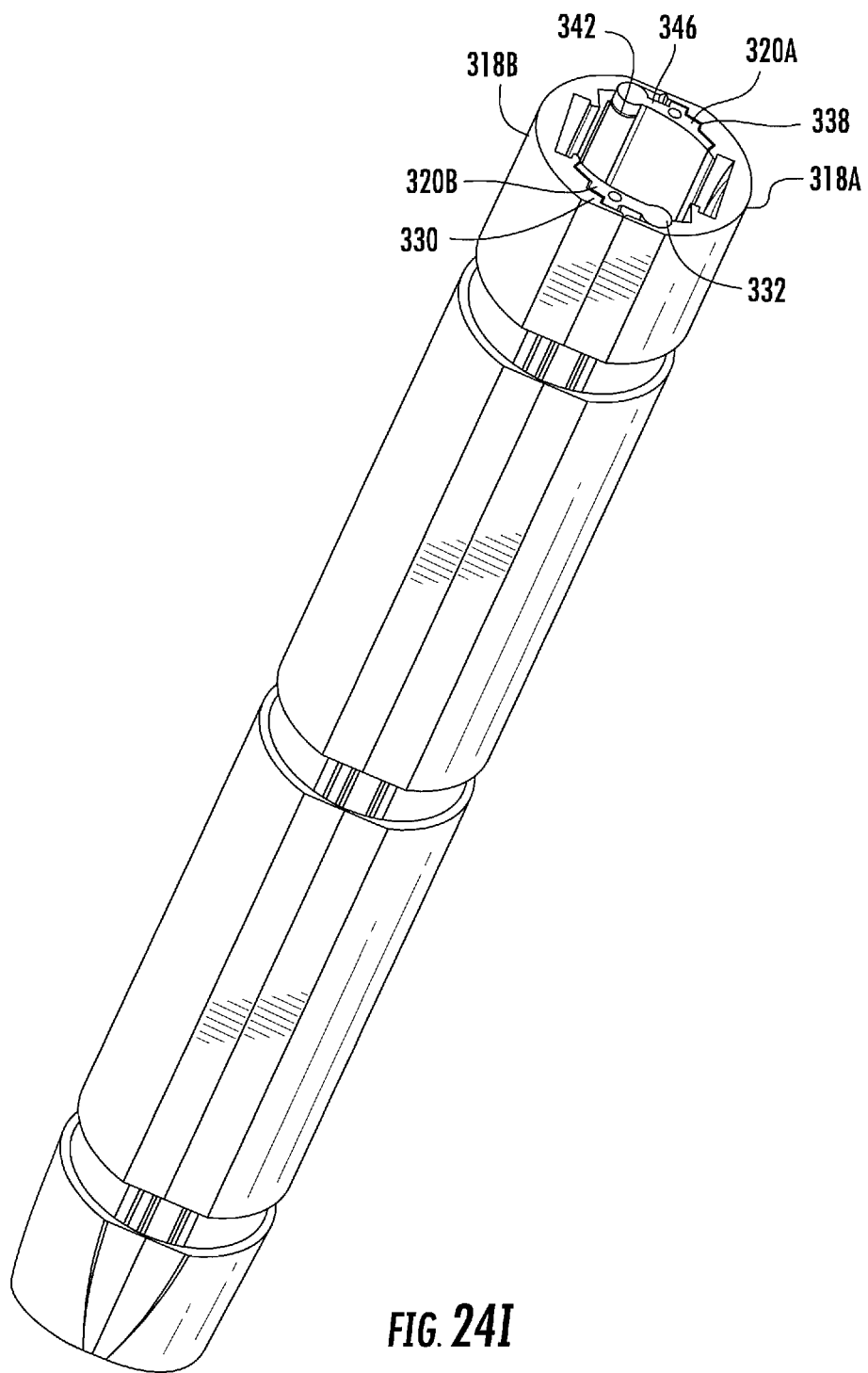
FIG. 24I is an alternative embodiment of the adjustable retractor illustrated in FIG. 24A.

The retractor 300 may be designed to include any feature taught for the various retractor described throughout the document. FIG. 24F illustrates the retractor 300 shown in FIG. 224A having insulated electrical conductors 16 positioned within internal track 362. The insulated electrical conductors 16 may be used, for example, to provide electrical pathways to provide nerve monitoring. An internal track 364 may be used for mounting fiber optical lights 18 to provide illumination of the surgical space located at the distal end of the retractor. To aid in any surgical procedure, a hand operated tool 366 may be configured to engage with the retractor 300, see FIG. 24G. The tool 366 includes an elongated body 368 having a first end 370 and a second opposing end 372. The second end 372 comprises a retractor engaging member 374 having an opening 376. The retractor engaging member 374. The retractor 300 may be configured to have an exterior surface adjacent configured to operatively engage a complimentary annular surface formed by the hand operated tool 300 whereby the elongate body can be rotated with the patient. As shown in FIG. 24I, surfaces 378A and 378B are sized and shaped to engage with elongated members 318A and 318B. Surfaces 380A and 380B are sized and shaped to engage with elongated members 320A and 320B.

FIG. 24I illustrates the retractor 300 as described above with the elongated members 320A and 2320B positioned in the interior portion. In this embodiment, the stepped surfaces 330 of elongated member 318A and the stepped surfaces 334 of elongated member 318A are positioned along the interior surface. In addition, semicircular recessed regions 332 and 336 are also positioned along the interior surface. The elongated member 320A contains the stepped surfaces 338 and the partial cylindrical member 342 positioned within the outer surface 346. The elongated member 320B contains the stepped surfaces 350 and the partial cylindrical member 354 positioned within the outer surface 358.

Figure 24J:
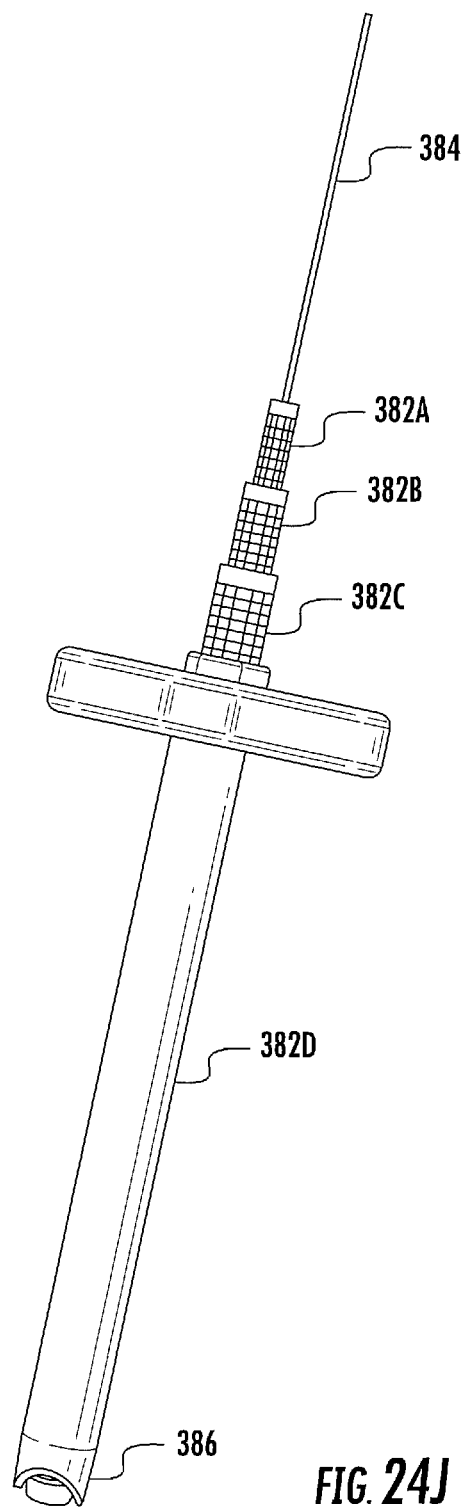
FIG. 24J is a perspective view of a series of initial dilators for use with the adjustable retractor illustrated in FIG. 24A or FIG. 24I.
Figure 24K:
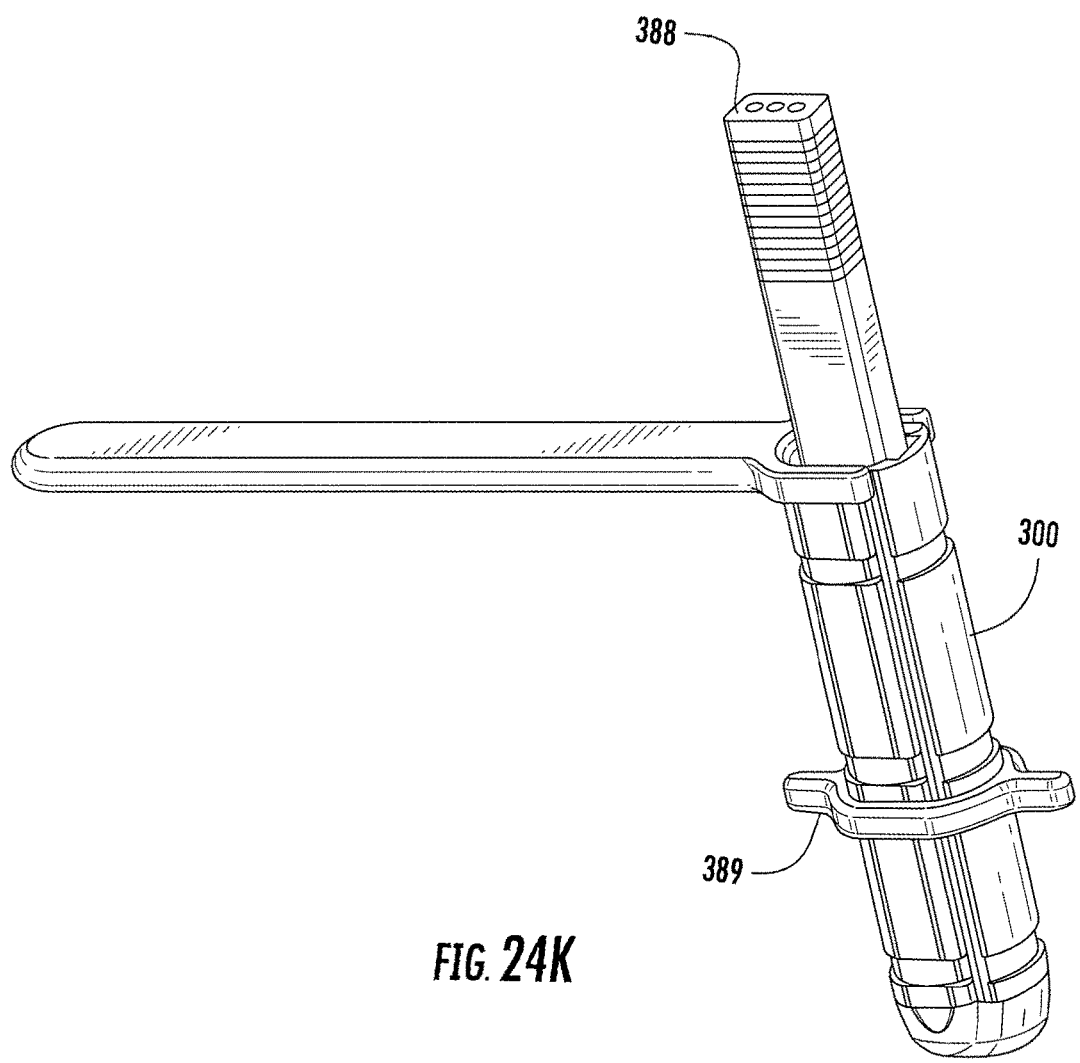
FIG. 24K is a top perspective view of an illustrative embodiment of a retractor shaped sequential dilator inserted into the adjustable retractor illustrated in FIG. 24A.
Figure 24L:
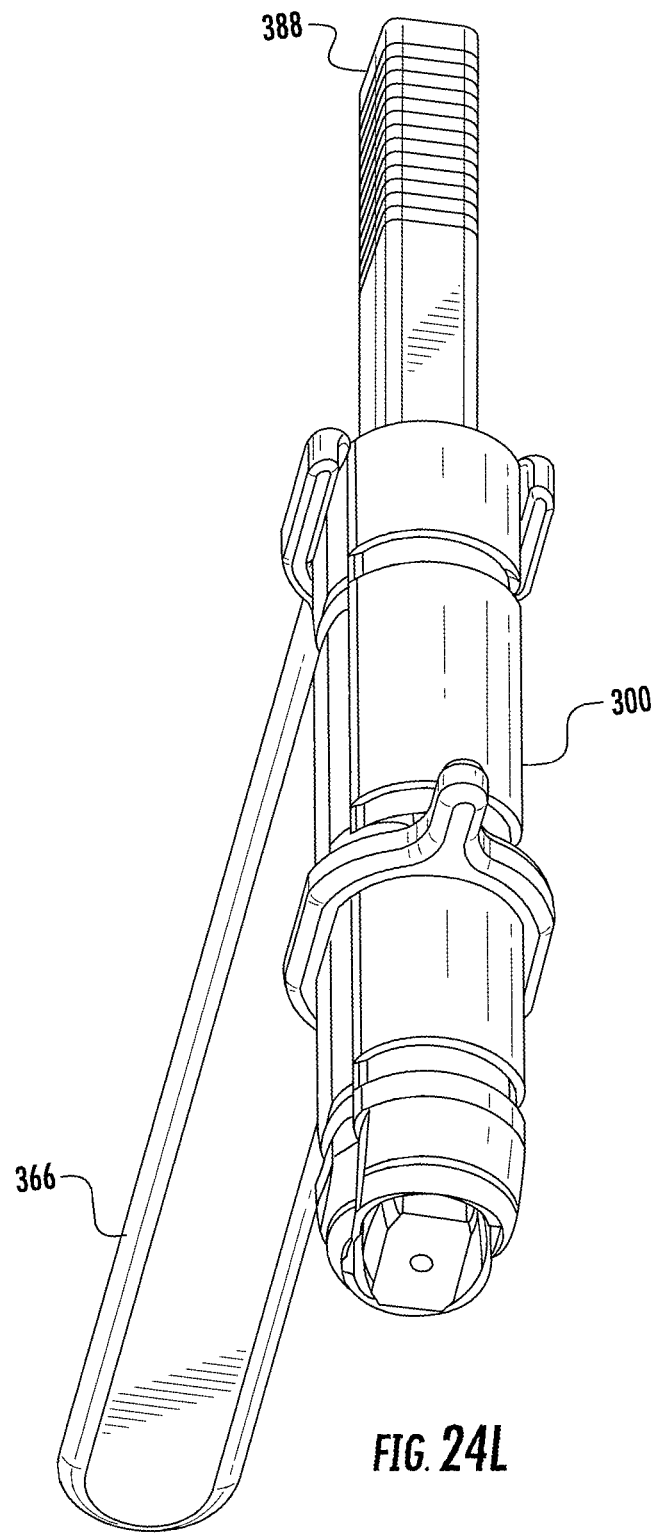
FIG. 24L is a bottom perspective view of the illustrative embodiment of a retractor shaped sequential dilator inserted into the adjustable retractor illustrated in FIG. 24A.

The retractors 300 illustrate in FIGS. 2A-25I are designed to be expanded using a plurality of dilators, including the dilators described previously. FIG. 24J illustrates a series of dilators that can be used to in the process of inserting retractor 300. In use, a k-wire 384 inserted into the initial 6 mm dilator 382A can be inserted through a skin incision. A second 9 mm dilator 382B is inserted over the first dilator 382A. A third dilator 282C, 12 mm, is then inserted over the all the second dilator 382B. All three dilators remain in place until the retractor 300 is slide over and properly placed. A retractor-shaped dilator 382D having a shape similar to, or the same as the retractor 300 may be used to aid in moving nerve fibers. Rotation of the retractor-shaped dilator 382D ninety degrees can function to disassociate final fibers on the spine. The retractor-shaped dilator 382D may have a distal end having a shape as described previously, such as for the embodiments illustrated in FIG. 18A, 18B, 19A, 19B, or 19C. The retractor 300 is then placed over the 4 inner dilators (382A-382D). Once the retractor is rotated and in place, the 4 inner dilators are removed. A retractor shaped sequential dilator 388 is then inserted into the retractor 300, see FIGS. 24K and 24L. The retractor shaped sequential dilator 388 is an elongated body having a shape that mirrors the shape of the inner surface of the retractor 300. For example, the retractor shaped sequential dilator 388 may be shaped or configured to mirror the shape or configuration of one or more of the elongated members 318A, 318B, 320A, and 320B. Such shape allows for expansion of the retractor 300 in one plane or the same direction the retractor 300 is designed to open. Inserting a plurality differently sized retractor shaped sequential dilators 388, such as a first retractor shaped sequential dilator having a 14 mm height× 16 mm length, followed by 14 mm×18 mm, 14 mm×20 mm, and 14 mm×24 mm ensures that that the retractor 300 opens in the single intended plane of opening. Retractor 300 may optionally include a key 389 (similar to tool 30) configured to couple to the outer surface. The key 389 is designed to provide a user an additional mechanism to rotate or reposition the retractor 300.

Figure 25:
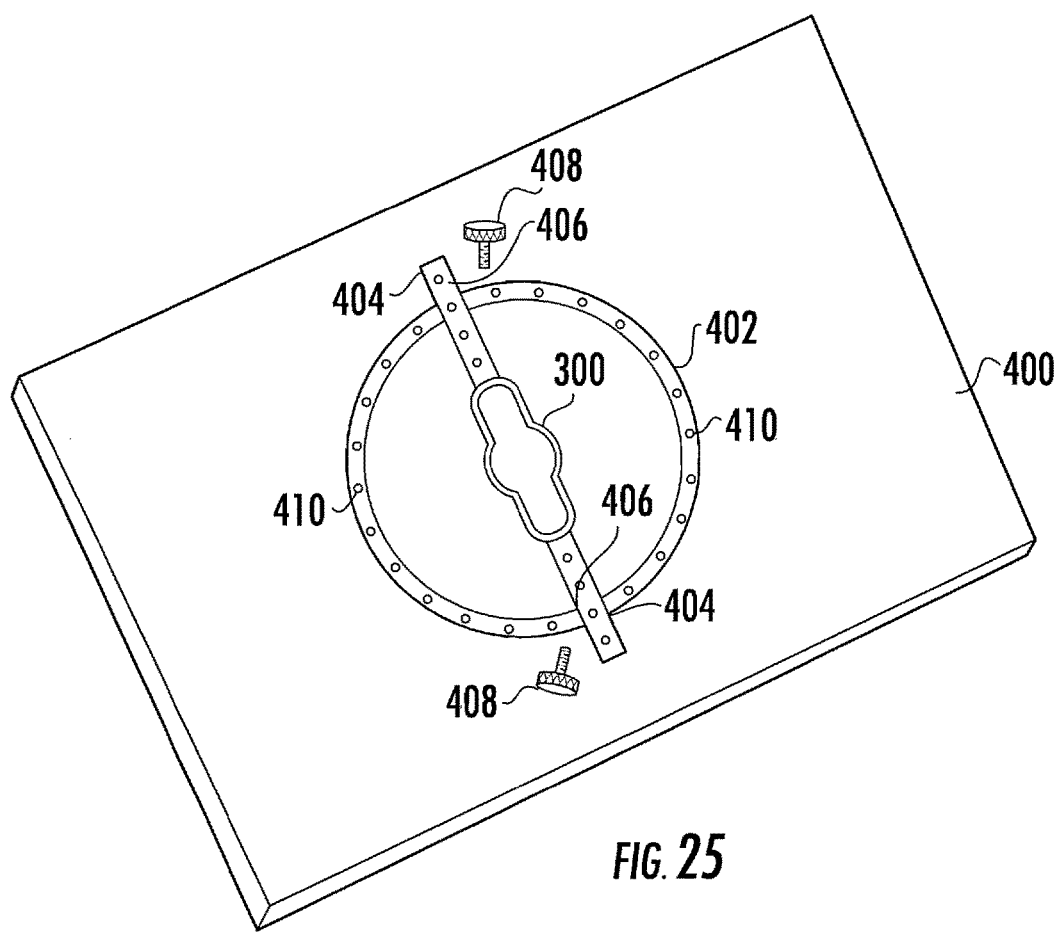
FIG. 25 is a perspective top view the retractor, the patient pad and a device to anchor the retractor to the patient pad.

FIG. 25 is a perspective top view of the retractor, the patient pad 400 and a device to anchor the retractor to the patient pad. Patient pad 400 is similar to pad 40, as described above, but further includes a hard ring 402, formed from metal or plastic, surrounding the retractor 300 that has been placed through the pad 400. A pair of tabs 404 extends from the proximal end of the retractor. The material for the tabs 404 is a more malleable composite of the material used for the retractor. The tabs 404 include holes or slots 406 that are configured to receive threaded thumb screws 408. Likewise, ring 402 includes holes and or slots 410 located around the circumference of the ring 402. Thumb screws 408 are passed through the appropriate apertures 406 in tabs 404 and are secured in the appropriate apertures 410 located on ring 402. The tabs can be positioned at the desired location along the ring. Then the thumbscrews are positioned in the proper apertures and tightened, whereby the tabs will hold the proximal end of the retractor at the desired angle.

Figure 26:
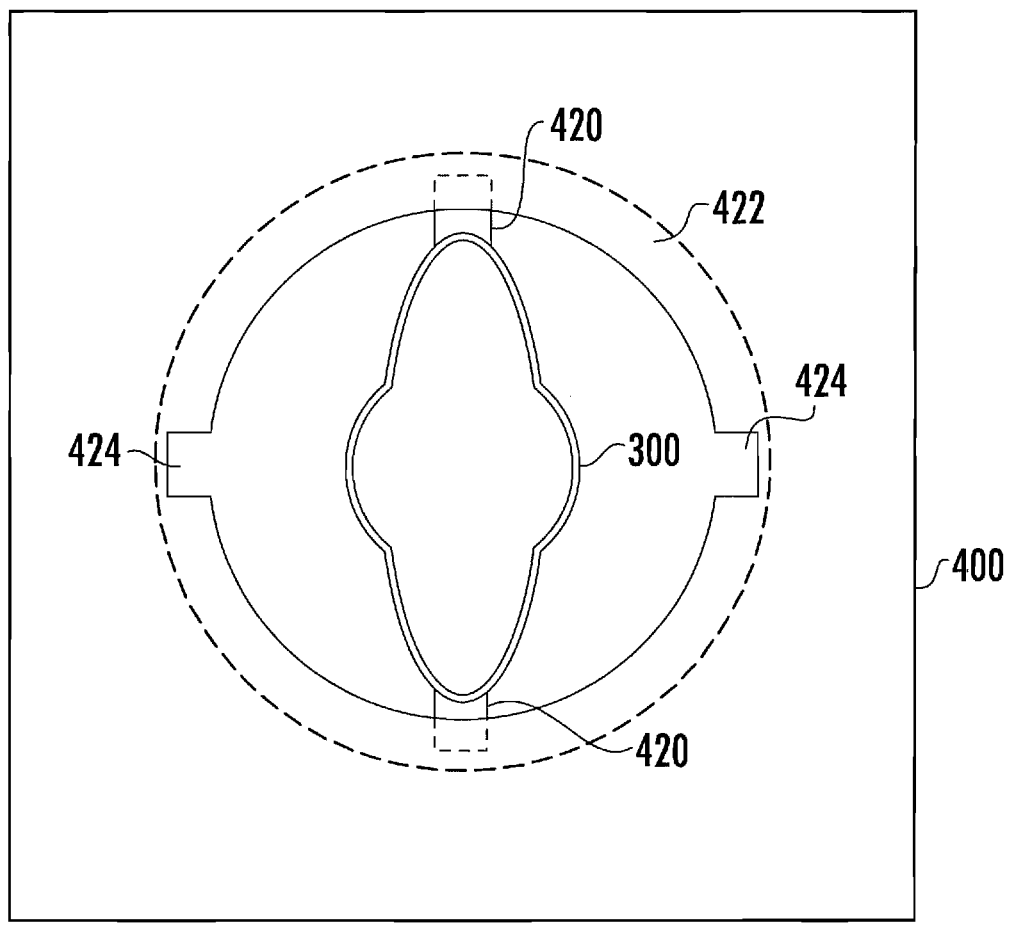
FIG. 26 is a top perspective view an alternative arrangement for anchoring the retractor to the patient pad.

FIG. 26 is a perspective view an alternative arrangement for anchoring the retractor 300 to the patient pad 400. In this embodiment the retractor 300 has a pair of radially projecting tabs 420 that are oriented in diametrically opposed relationship. Patient pad 400 includes an annular recess or groove 422 formed either within or recessed on the bottom side of the pad. Located on the upper surface of patient pad 400 is a pair of diametrically opposed slots 424 that extend from the upper surface to the groove or recess 422. To anchor the retractor, each of the tabs 420 is brought into alignment with a slot 424. After each tab 420 is positioned within groove 422 the retractor is rotated with respect to the pad thereby effectively anchoring the retractor 300.

Figure 27:
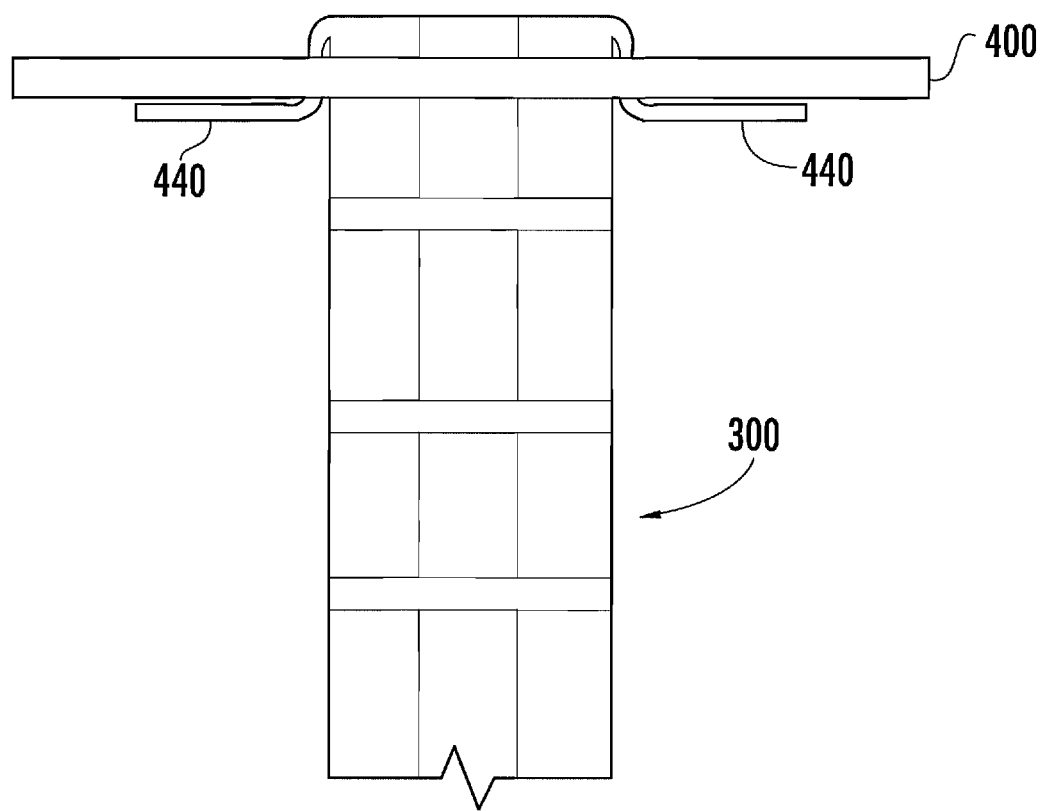
FIG. 27 is a side perspective view of another alternative embodiment to anchor the retractor to the patient pad.

FIG. 27 is a perspective view of another alternative embodiment to anchor the retractor to the patient pad. In this embodiment tabs 440 extend from the proximal aspect of the retractor 300 in diametrically opposed orientation. The tabs 440 are made from a malleable plastic material. As shown in FIG. 27 the tabs fold along the edge of the retractor 300 and the pad 400 is placed over the retractor 300. The retractor extends through the pad 400 through a slit formed therein while the tabs are positioned beneath the pad 400. The tabs maintain a downward force on the retractor with the constant pressure applied from the patient pad that is in contact with the patient's skin.

Figure 28:
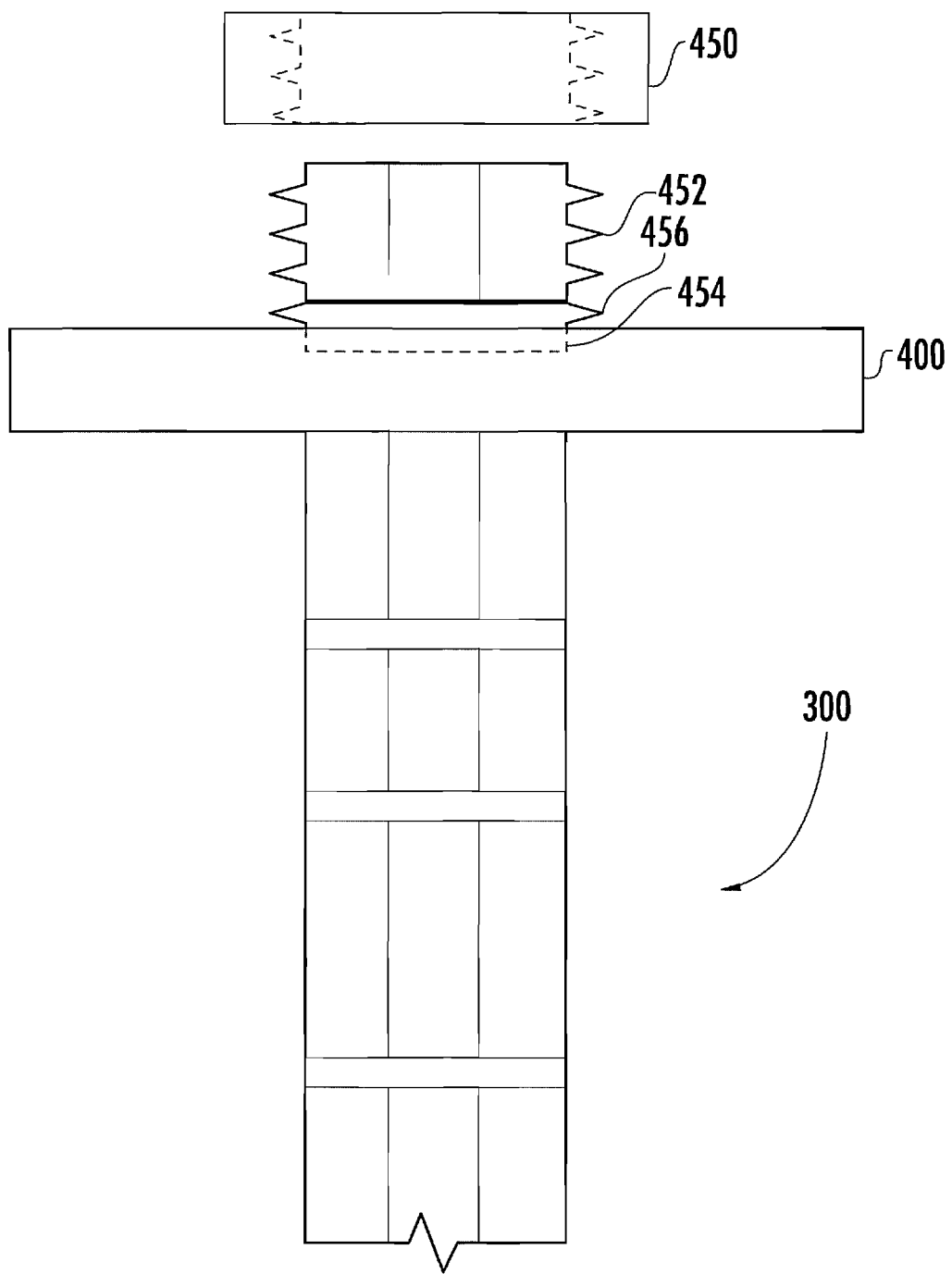
FIG. 28 is a side perspective view of yet another alternative embodiment to anchor the retractor to the patient pad.

FIG. 28 is a perspective view of yet another alternative embodiment to anchor the retractor to the patient pad. In this embodiment the proximal aspect of the retractor 300 includes a series of coarse threads 452 formed on the exterior surface of the retractor. The patient pad 400 includes ring 454 embedded in the upper surface of the patient pad 400. The exterior surface of ring 454 includes thread 456 configured with the same coarse thread dimension as threads 452. An internally threaded annular ring 450 is used to secure the retractor to the patient pad. The internal threads of annular ring 450 are sized and configured to threadably engage threads 452 on the retractor and thread 456 on the embedded ring 454. The retractor is placed through an opening in pad 400 and the annular ring 450 is placed over the retractor 300. As the ring is tightened it applies a downward force to the retractor's proximal end to maintain the desired depth of the distal tip in the patient's tissue.

Figure 29:
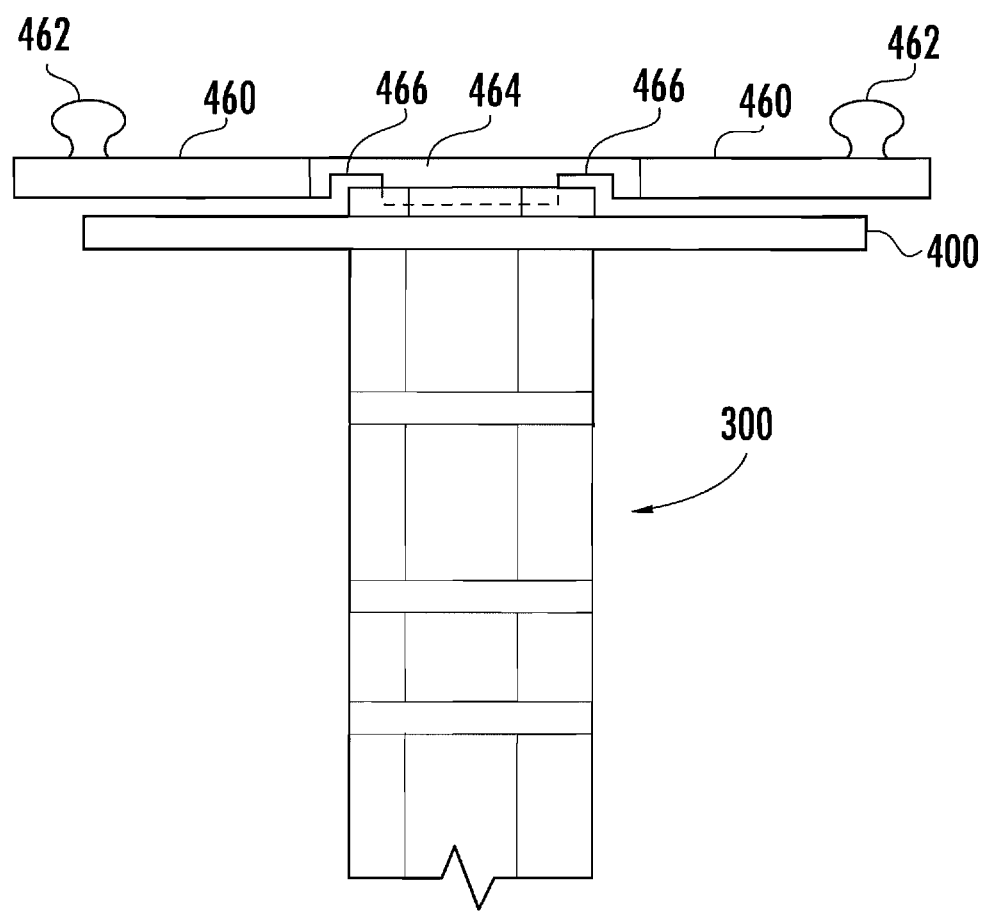
FIG. 29 is a side perspective view of a retractor including a handle to manually stabilize the retractor in the patient.

FIG. 29 is a perspective view of a retractor including a handle to manually stabilize the retractor in the patient. In this embodiment the proximal aspect of the retractor 300 cooperates with a manual anchoring device that includes an annular member 464 with a pair of diametrically opposed arms 460 extending radially outward from annular member 464. The bottom surface of annular member 464 includes an annular groove 466. Annular groove 466 is comprised of a series of semi elliptical segments, configured to mate with the upper surface of the retractor 300, and having sufficient width so as to be able to cooperate with the upper peripheral edge of retractor 300 either in its compact, intermediate or expanded condition. Arms 460 and annular member 464 are formed from a rigid material such as a rigid plastic or metal. Each arm includes a gripping element 462. As shown, the gripping element is a ball type handle however any other type of handle mechanism such as a vertical post, or "T" or loop configuration would be acceptable. The retractor 300 would be physically stabilized by an individual grasping and holding either one or both of the gripping elements 462 in a fixed position. Alternatively, one could use the hand stabilized retractor without the aid of the patient pad 400.

FIGS. 30-39 illustrate a system for providing access to a surgical location within a patient comprising one or more of a retractor, such as retractor 300 having the features described above, a shim 464, and a shim delivery device, such as a shim handle 466. The shim 464 is designed to provide stability when used with the retractor 300 and provide fixation at the distal end or at the proximal end. The shim 464 is configured to engage and fit or secure within at least a portion of the retractor 300. Referring to FIGS. 30 and 31, the shim 464 comprising a first end 468, a second end 470, and a main body 472 extending therebetween. The first end 468 is configured to engage with the handle 466 and comprises a handle engaging member 474, illustrated herein as a generally planar surface 476 extending away from the main body 472. The second end 470 comprises a tapered portion 478 and is configured to engage with a portion of a disc, such as the disc annulus. The main body 472 comprises a length that is sufficient to extend the length of, and out past the distal end of the retractor 300. Accordingly, the length of the shim 464 is greater than the length of the retractor for which it engages. The length of the sham can be designed to be sufficient, that when used whit he retractor 300, the second end 470 can extend incise the lateral aspect of the annulus of the disc, and extend into the disc itself. Depending in the need of use, the length can be vary to allow for insertion just inside the annulus to a length that can cross to the contra-lateral annulus, or anywhere inbetween. The main body 472 further comprises an outer surface 480 and an inner surface 482. The shim 464 may also be configured to be mountable to a table. In such an embodiment, the first end 468 may contain a threaded opening 484, see FIG. 32.

Figure 33:
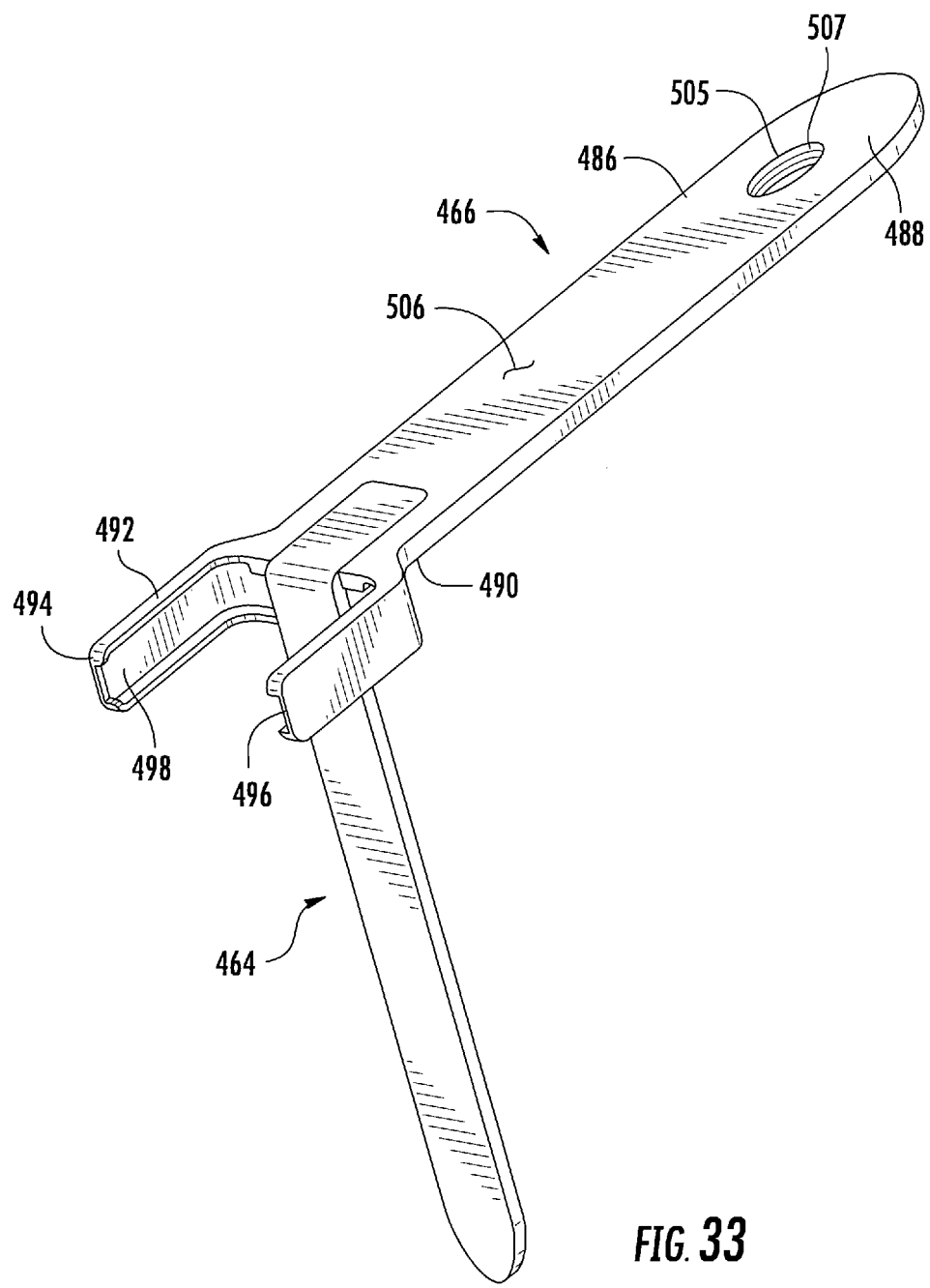
FIG. 33 is a perspective view of the retractor shim secured to a handle.
Figure 34:
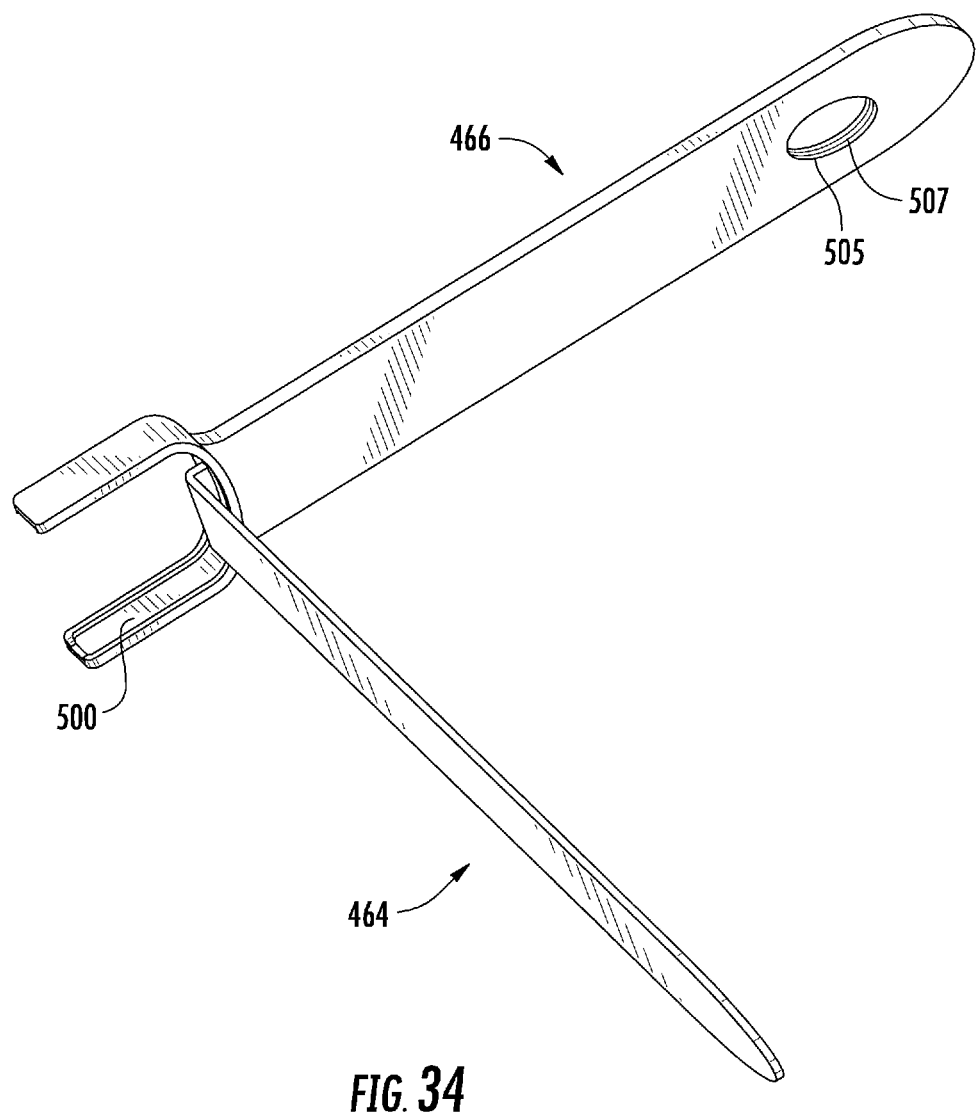
FIG. 34 is an alternative view of the retractor shim with handle illustrated in FIG. 33.
Figure 35:
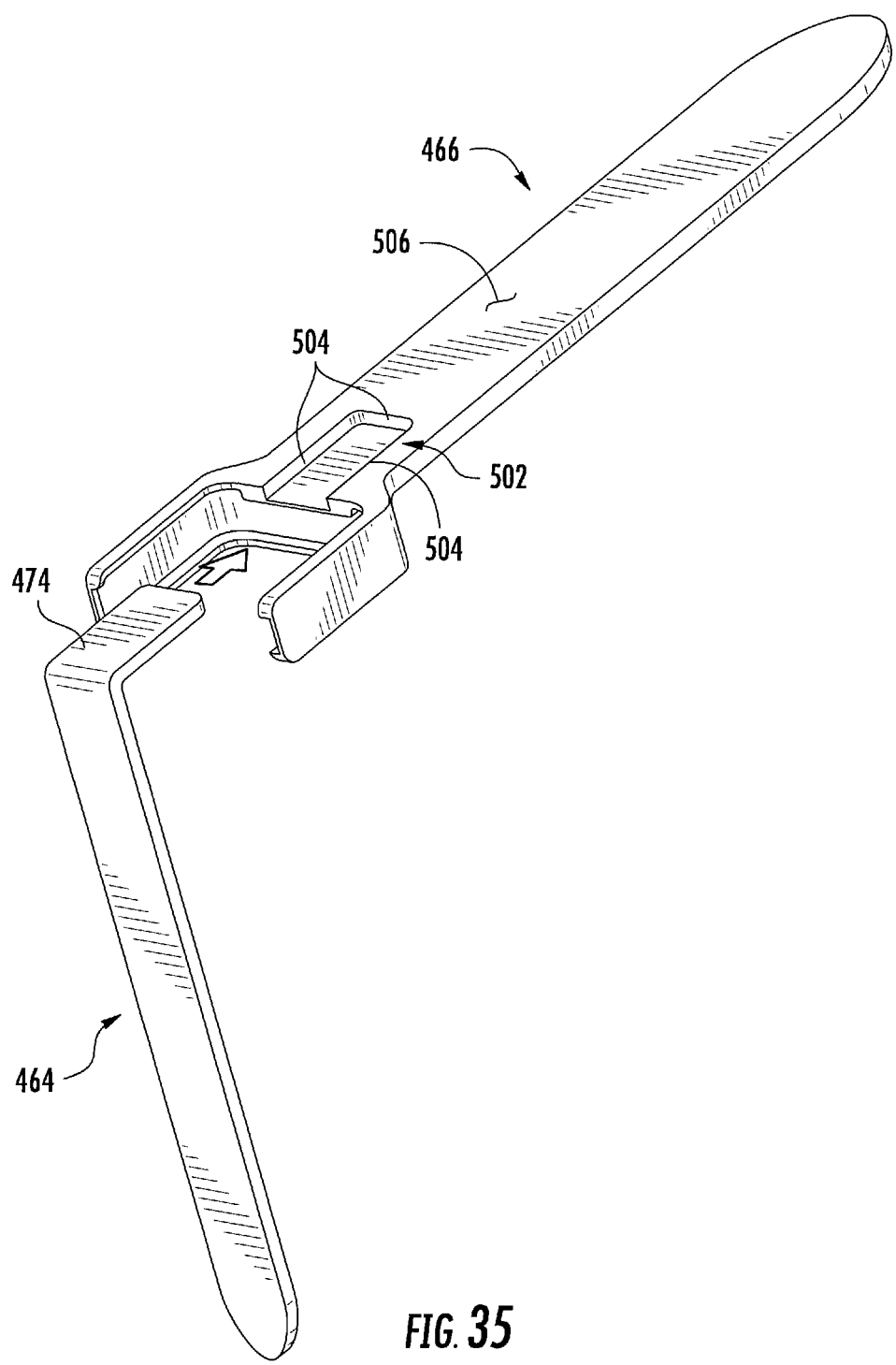
FIG. 35 illustrates the shim removed from the handle.

Referring to FIGS. 33 and 34, perspective views of the shim handle 466 with the shim 464 secured thereto are shown. The shim handle 466 contains a main body 486 having a first end 488 sized and shaped to allow a user, such as a surgeon, to grip, hold, and maneuver with his/her hand, and a second end 490 having a retractor body engaging member 492. The retractor body engaging member 492 comprises two arm members, 494 and 496 extending out from the main body 486. Internal surfaces 498 and 500 are sized and shaped to engage with the body of retractor 300. The shim 464 may be removably secured to the shim handle 466 at shim receiving area 502. As illustrated in FIG. 35, the shim receiving area 502 is a partially cutout portion of the handle main body 486 and may include channels 504 sized and shaped to receive, and secure thereto, the handle engaging member 474. The handle engaging member 474 may include ridged or overhang portions configured to engage with channels 504. Alternatively, a portion of the handle engaging member 474 may simply engage with the shim receiving area 502 through frictional or snap fit mechanism. Preferably, the partially cut out shim receiving area 502 has a cut out depth so that when the handle engaging member 474 is engaged, a generally planar surface is formed and is flush with the main body outer surface 506. The shim handle 466 may also be designed to be secured to a table. Referring to FIGS. 33 and 34, the shim handle main body 486 may contain, but need not, an aperture 505 with threading 507 to aid in proximal end fixation.

Figure 36:
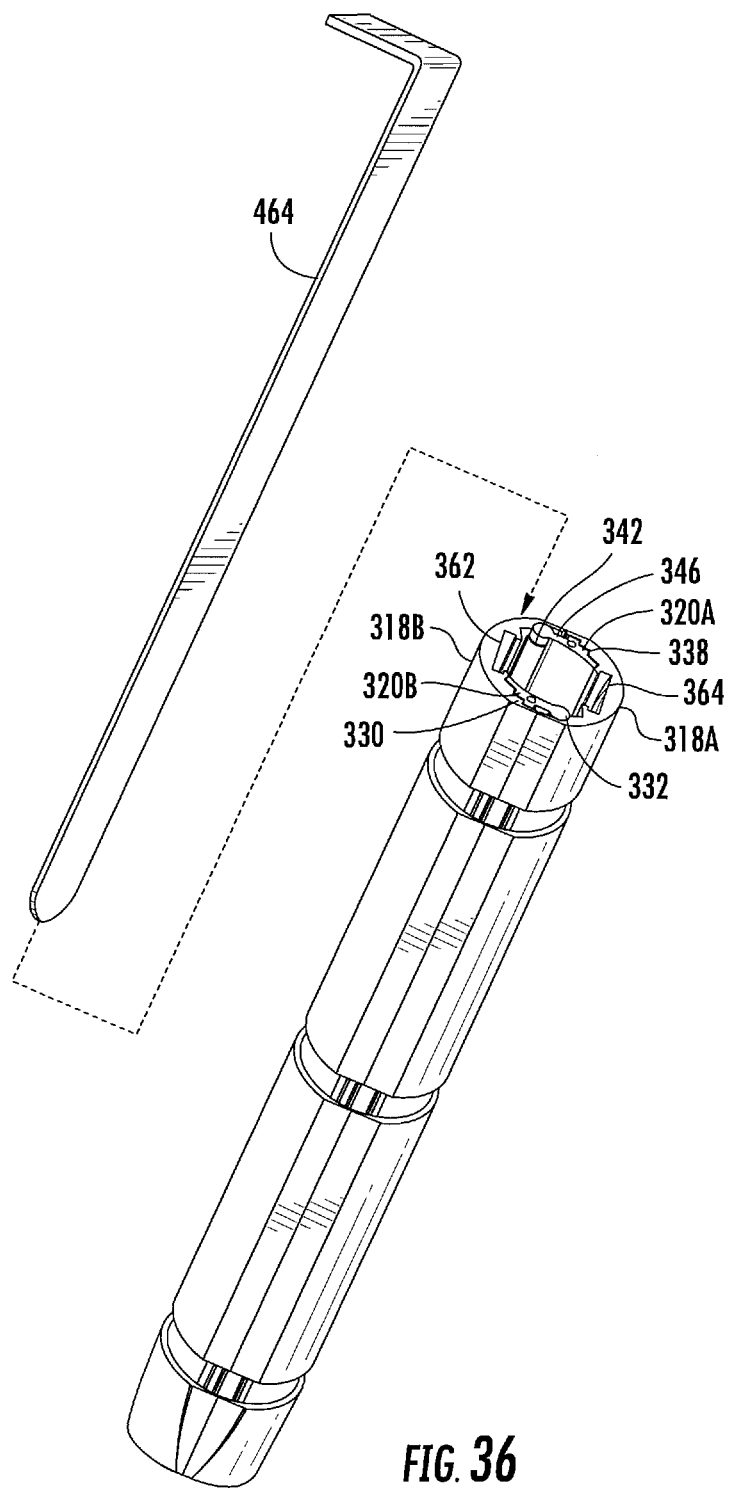
FIG. 36 illustrates a system for providing access to a surgical location within a patient, the system including a retractor and shim.
Figure 37:
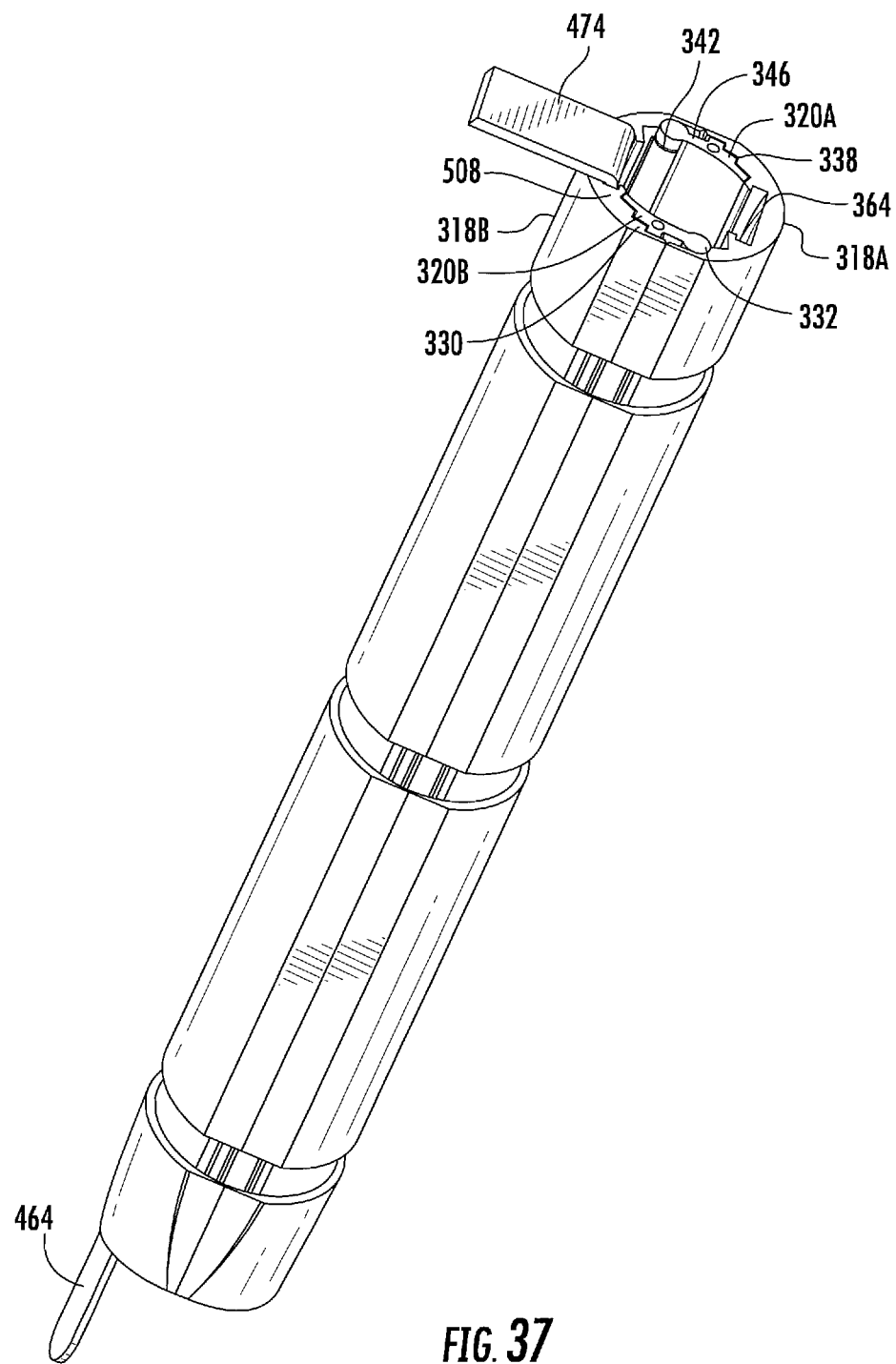
FIG. 37 illustrates the system for providing access to a surgical location within a patient in which a shim is inserted into and engages with a retractor body.
Figure 38:
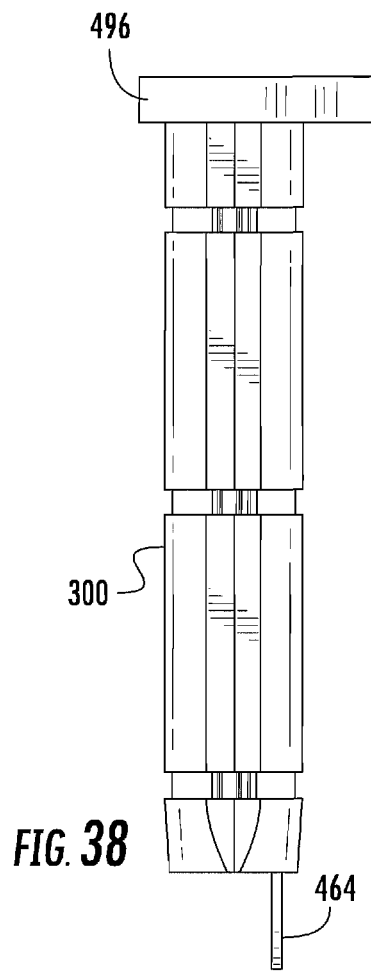
FIG. 38 is a side view of the retractor body with shim insertion with use of a handle.
Figure 39:
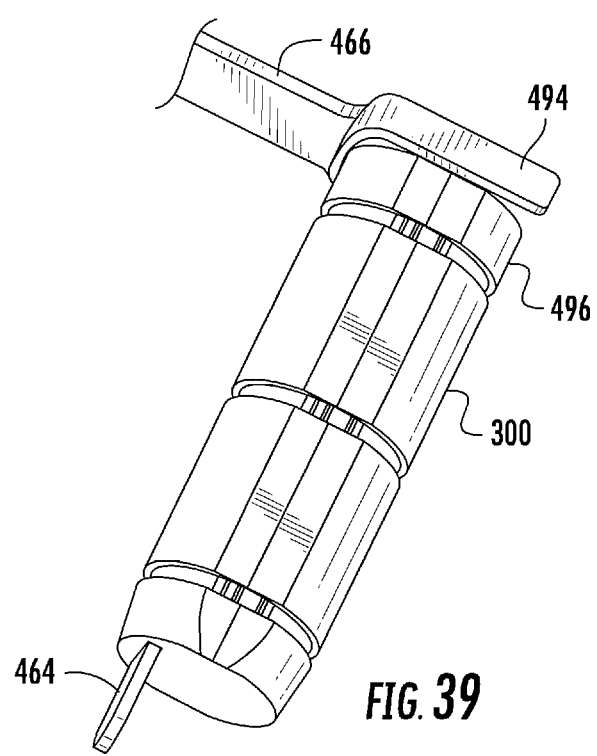
FIG. 39 is a bottom view of the retractor body with shim insertion illustrated in FIG. 38.

FIGS. 36-39 illustrate the shim 464, and the shim handle 466 with the shim 464 engaging with the retractor 300. As illustrated in FIG. 36, the shim 464 is designed to engage the retractor 300 through insertion into the internal track 362 or 364. Once inserted, the handle engaging member 474 may rest on the external surface 508 of the retractor 300. As described previously, a portion of the shim 464 extends out past the distal end of the retractor 300. FIGS. 38 and 39 illustrate the use of the shim handle 466 for engaging the shim 464 with the retractor 300. By having a main body that extends the length of the retractor, and having a distal tip that extends there past, the shim 464 provides the functionality of fixation, preventing the retractor from moving (particularly in an up or down direction), and stability. The shim 464 can provide distal fixation as the distal tip 478 extends out past the retractor 300 and can therefore extend into the annulus. The shim 464 also provides proximal fixation as the shim 464 can either secure directly to a surface using opening 484, or when affixed to the handle, the user can grab onto the handle or the handle can be secured directly to a surface through aperture 505. In either method, the shim 464 can be fixed at the proximal end to a surface or a user's hand.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A system for providing access to a surgical location within a patient comprising:
an elongated body comprised of a plurality of segments, said plurality of segments include a first pair of elongated members and a second pair of elongated members arranged oppositely about each other, said first pair of elongated members including a first elongated member having a surface having a first set of stepped surfaces and one first recessed channel running parallel to a longitudinal axis and a second elongated member having a surface having a second set of stepped surfaces and one second recessed channel running parallel to said longitudinal axis, said second pair of elongated members including a third elongated member having a surface having a third set of stepped surfaces and a first recessed channel engaging member and a fourth elongated member having a surface having a fourth set of stepped surfaces and a second recessed channel engaging member, said first pair of segments hingedly cooperating with said second pair of elongated members along one surface and cooperating with said second pair of elongated members in an interdigiting manner along a second surface.

2. The system for providing access to a surgical location within a patient according to claim 1 further including a shim, said shim configured to removeably engage with at least one portion of said elongated body.

3. The system for providing access to a surgical location within a patient according to claim 1 wherein said shim comprises a body length that is greater than a length of said elongated body.

4. The system for providing access to a surgical location within a patient according to claim 2 wherein said at least one portion of said elongated body configured to engage with said shim includes at least one internal track.

5. The system for providing access to a surgical location within a patient according to claim 1 further including:
at least one elastomeric member surrounding said plurality of segments and exerting a radially directed inward force against the outer surface of each said plurality of segments.

6. The system for providing access to a surgical location within a patient according to claim 1 wherein said first pair of elongated members are arranged oppositely about a first plane formed substantially perpendicular to said longitudinal axis, and said second pair of elongated members are arranged oppositely about a second plane, said second plane having a different orientation about said longitudinal axis than said first plane.

7. The system for providing access to a surgical location within a patient according to claim 6 wherein the cross section of the first elongated members of said first pair of elongated members is different than the cross section of the elongated members of said second pair of elongated members.

8. The system for providing access to a surgical location within a patient according to claim 1 wherein an outwardly directed surface on each of said elongated members includes at least one circumferentially orientated recess to retain said at least one elastomeric member.

9. The system for providing access to a surgical location within a patient according to claim 1, wherein each of said stepped surfaces extend the length of the said elongated segments from the proximal end portion to the distal end portion.

10. The system for providing access to a surgical location within a patient according to claim 1, wherein said plurality of segments are made from a radiolucent material.

11. The system for providing access to a surgical location within a patient according to claim 1, wherein one or more of said segments include an electrically insulated conductor which extends from the proximal end portion to the distal end portion, whereby electrical pathways are established to provide nerve monitoring.

12. The system for providing access to a surgical location within a patient according to claim 1, wherein one or more of said segments include one or more radio opaque markers, thereby enabling visualization of said device under fluoroscopy.

13. The system for providing access to a surgical location within a patient according to claim 1, wherein one or more of said segments include at least one screw hole extending from the top surface portion to the distal surface portion and adapted to receive a screw to fasten said device to a bone within said patient.

14. The system for providing access to a surgical location within a patient according to claim 1, wherein one or more of said segments has an exterior surface adjacent said top portion thereof that is configured to operatively engage a complimentary annular surface formed on a hand operated tool, whereby the elongate body can be rotated with the patient.

15. The system for providing access to a surgical location within a patient according to claim 1 further including a pad configured for selective attachment to the patient and having a slit that conforms to the shape of the elongated body at the top portion thereof to frictionally engage and firmly anchor said device in a fixed position relative to said patient.

16. The system for providing access to a surgical location within a patient according to claim 15, further including an anchoring device attached to the proximal end portion of said elongate body and to said pad.

17. The system for providing access to a surgical location within a patient according to claim 16, wherein said anchoring device includes a hard ring on the upper surface of said pad, and said elongate member includes a pair of tabs extending there from, said hard ring and said tabs including a plurality of apertures, and a pair of thumb screws sized and configured to selectively engage the apertures formed in said hard ring and said tabs for adjustably securing said tabs to said ring and anchoring said elongated member to said pad.

18. The system for providing access to a surgical location within a patient according to claim 15, wherein said anchoring device includes a pair of radially projecting tabs that are oriented in diametrically opposed relationship on said elongated body, and a groove formed beneath an upper surface of said pad and a pair of diametrically opposed slots on said pad that extend from the upper surface of said pad to said groove, said tabs being secured in said groove upon insertion into said slots and rotation of said elongated body.

19. The system for providing access to a surgical location within a patient according to claim 16, wherein said anchoring device includes a plurality of malleable tabs that extend from the proximal aspect of the elongated body and are folded along the edge thereof and through a slit formed in the pad and positioned beneath the pad, whereby the tabs maintain a downward force on the retractor with the constant pressure that is applied from the pad.

20. The system for providing access to a surgical location within a patient according to claim 16, wherein said anchoring device includes a threaded exterior surface on the proximal end of the elongated body, an annular insert molded into said pad having an external thread that is sized and configured to match the threaded exterior surface, and an annular retaining ring having an internal thread that is configured to threadably engage the threaded exterior surface on the elongated body and the external thread of the molded insert, whereby as the annular retaining ring is threaded downward, it anchors the elongated body to the pad.

21. The system for providing access to a surgical location within a patient according to claim 16, wherein said anchoring device includes a plurality of arms extending radially outward from an annular member, the proximal end of the elongated body cooperating with an annular groove formed on a bottom surface of said annular member, said arms connected to the elongated body at one end and including a manual gripping element adjacent the opposite end of each arm, whereby the elongated body is physically stabilized by manually holding at least one of said gripping elements.

22. The system for providing access to a surgical location within a patient according to claim 1 further including an anchoring device, said anchoring device including a plurality of arms extending radially outward from an annular member, the proximal end of the elongated body cooperating with an annular groove formed on a bottom surface of said annular member, said arms connected to the elongated body at one end and including a manual gripping element adjacent the opposite end of each arm, whereby the elongated body is physically stabilized by manually holding at least one of said gripping elements.

23. The system for providing access to a surgical location within a patient according to claim 1, wherein one or more of said segments has an exterior surface adjacent said top portion thereof that is configured to operatively engage a complimentary annular surface formed on a hand operated tool whereby the elongate body can be rotated with the patient.

24. The system for providing access to a surgical location within a patient according to claim 1 further including a handle, said handle configured to secure to said shim.

25. The system for providing access to a surgical location within a patient according to claim 1 where said shim is configured to be secured to a surface.

26. A system for providing access to a surgical location within a patient, said system comprising:
an elongated body comprised of a plurality of segments, said plurality of segments include a first pair of elongated members arranged oppositely about a first plane formed substantially perpendicular to a longitudinal axis, said first pair of elongated members including a first elongated member having an outer surface having a first set of stepped surfaces and one first recessed channel running parallel to a longitudinal axis and a second elongated member having an outer surface having a second set of stepped surfaces and one second recessed channel running parallel to said longitudinal axis;

a second pair of elongated members arranged oppositely about a second plane, said second plane having a different orientation about said longitudinal axis than said first plane, said first and second pairs of elongated members selectively engaged to provide radial separation along each said plane, said second pair of elongated members including a third elongated member having an inner surface having a third set of stepped surfaces and a first recessed channel engaging member and a fourth elongated member having an inner surface having a fourth set of stepped surfaces and a second recessed channel engaging member; and a shim, said shim configured to removeably engage with at least one portion of said elongate body.

27. The system for providing access to a surgical location within a patient according to claim 26 wherein said shim comprises a body length that is greater than a length of said elongated body.

28. The system for providing access to a surgical location within a patient according to claim 26 further including a handle, said handle configured to secure to said shim.

29. The system for providing access to a surgical location within a patient according to claim 26 where said shim is configured to be secured to a surface.

30. The system for providing access to a surgical location within a patient according to claim 26 further including an elastomeric pad configured to be affixed to said patient and having a slit that conforms to an outer surface of said elongated body adjacent the proximal end portion.

31. The system for providing access to a surgical location within a patient according to claim 26 further including an anchoring device connecting said elongated body to said pad, said anchoring device having a first member formed in the upper portion of said elastomeric pad and a second member extending from said proximal end of said elongated body; whereby the elongated body is frictionally engaged by the pad and is firmly anchored to a position that is fixed relative to said patient.

32. The device for providing access to a surgical location within a patient according to claim 26 wherein each said stepped surface extends the length of the said elongated segments from said proximal end to said distal end.

33. The device for providing access to a surgical location within a patient according to claim 26, further including a plurality of elastomeric members surrounding said plurality of segments and exerting a radially directed inward force against the outer surface of each said plurality of segments.

34. A system for providing access to a surgical location within a patient, said device comprising:

an elongated body comprised of a plurality of segments, said plurality of segments include a first pair of elongated members and a second pair of elongated members arranged oppositely about each other;

said first pair of elongated members including a first elongated member having a surface having a first set of stepped surfaces extending a length of said elongated member from said proximal end to said distal end and one first recessed channel running parallel to a longitudinal axis and a second elongated member having a surface having a second set of stepped surfaces extending a length of said elongated member from said proximal end to said distal end and one second recessed channel running parallel to said longitudinal axis;

said second pair of elongated members including a third elongated member having a surface having a third set of stepped surfaces extending a length of the said elongated member from said proximal end to said distal end and a first recessed channel engaging member and a fourth elongated member having a surface having a fourth set of stepped surfaces extending a length of said elongated member from said proximal end to said distal end and a second recessed channel engaging member, said first pair of elongated segments hingedly cooperating with said second pair of elongated members along one surface and cooperating with said second pair of elongated members in an interdigiting manner along a second surface; and a shim, said shim configured to removeably engage with at least one portion of said elongate body.

35. The system for providing access to a surgical location within a patient according to claim 34 wherein said shim comprises a body length that is greater than a length of said elongated body.

36. The system for providing access to a surgical location within a patient according to claim 34 further including a handle, said handle configured to secure to said shim.

37. The system for providing access to a surgical location within a patient according to claim 34 where said shim is configured to be secured to a surface.

* * * * *